US011964294B2

(12) United States Patent
Ueda et al.

(10) Patent No.: US 11,964,294 B2
(45) Date of Patent: Apr. 23, 2024

(54) MIST-GENERATING DEVICE

(71) Applicant: Panasonic Intellectual Property Management Co., Ltd., Osaka (JP)

(72) Inventors: Mitsuhiko Ueda, Osaka (JP); Tatsuya Kiriyama, Osaka (JP); Hiroaki Tachibana, Osaka (JP); Shogo Shibuya, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 644 days.

(21) Appl. No.: 17/258,005

(22) PCT Filed: Jun. 25, 2019

(86) PCT No.: PCT/JP2019/025246
§ 371 (c)(1),
(2) Date: Jan. 5, 2021

(87) PCT Pub. No.: WO2020/012954
PCT Pub. Date: Jan. 16, 2020

(65) Prior Publication Data

US 2021/0229120 A1 Jul. 29, 2021

(30) Foreign Application Priority Data

Jul. 10, 2018 (JP) ................................ 2018-131081
Jul. 10, 2018 (JP) ................................ 2018-131091
Dec. 12, 2018 (JP) ................................ 2018-232709

(51) Int. Cl.
*A61L 9/00* (2006.01)
*A61L 9/14* (2006.01)
(Continued)

(52) U.S. Cl.
CPC ................ *B05B 5/057* (2013.01); *A61L 9/14* (2013.01); *B01J 13/046* (2013.01);
(Continued)

(58) Field of Classification Search
CPC ...... A23L 29/256; A23L 33/105; A23P 10/30; A61K 9/5036; B01J 13/043
(Continued)

(56) References Cited

U.S. PATENT DOCUMENTS

2011/0123680 A1 5/2011 Tanaka et al.
2011/0206771 A1 8/2011 Choi et al.

FOREIGN PATENT DOCUMENTS

CN 1244893 2/2000
CN 101316628 12/2008
(Continued)

OTHER PUBLICATIONS

International Search Report issued in International Pat. Appl. No. PCT/JP2019/025246, dated Oct. 1, 2019, along with an English translation thereof.

(Continued)

*Primary Examiner* — Monzer R Chorbaji
(74) *Attorney, Agent, or Firm* — GREENBLUM & BERNSTEIN, P.L.C.

(57) ABSTRACT

A mist-generating device includes: a droplet generating unit that generates, in a third liquid, a functional droplet including a first liquid that is spherical and a second liquid that covers an entirety of the first liquid and has a volatility lower than a volatility of the first liquid; and a mist-generating unit that generates a multilayer mist obtained by atomizing the third liquid containing the functional droplet.

9 Claims, 15 Drawing Sheets

(51) Int. Cl.

| | |
|---|---|
| ***B01J 13/04*** | (2006.01) |
| ***B05B 5/025*** | (2006.01) |
| ***B05B 5/057*** | (2006.01) |
| ***B05B 7/06*** | (2006.01) |
| ***B05B 7/08*** | (2006.01) |
| ***B05B 12/14*** | (2006.01) |
| ***B05B 17/06*** | (2006.01) |

(52) U.S. Cl.
CPC ............ *B05B 5/0255* (2013.01); *B05B 7/061* (2013.01); *B05B 7/0846* (2013.01); *B05B 12/1472* (2013.01); *B05B 17/0615* (2013.01); *A61L 2209/134* (2013.01); *Y10T 428/2984* (2015.01)

(58) Field of Classification Search
USPC .......................................... 422/127–128, 306
See application file for complete search history.

(56) References Cited

FOREIGN PATENT DOCUMENTS

| | | | |
|---|---|---|---|
| CN | 102014871 | 4/2011 | |
| CN | 102202657 | 9/2011 | |
| CN | 102574078 | 7/2012 | |
| CN | 202290376 | 7/2012 | |
| JP | 2001-190943 | 7/2001 | |
| JP | 2012-065979 | 4/2012 | |
| WO | 98/021307 | 5/1998 | |
| WO | 2007/011866 | 1/2007 | |
| WO | 2008/121342 | 10/2008 | |
| WO | 2010/010902 | 1/2010 | |
| WO | WO-2010010902 A1 * | 1/2010 | ........... A23L 29/256 |
| WO | 2011/028764 | 3/2011 | |

OTHER PUBLICATIONS

Official Communication Received in Chinese Patent Application No. 201980045606.8, dated Nov. 23, 2021, along with an English translation thereof.

Official Communication Received in Chinese Patent Application No. 201980045606.8, dated Jun. 2, 2022.

* cited by examiner

MIST-GENERATING DEVICE

CROSS-REFERENCE TO RELATED APPLICATIONS

Pursuant to 35 U.S.C. § 371, this application is the United States National Stage Application of International Patent Application No. PCT/JP2019/025246, filed Jun. 25, 2019, which claims priority to Japanese Application Nos. JP 2018-232709, filed Dec. 12, 2018, JP 2018-131091, filed Jul. 10, 2018, JP 2018-131081, filed Jul. 10, 2018. The disclosure of each of these applications is herein incorporated by reference in its entirety.

TECHNICAL FIELD

The present invention relates to a mist-generating device.

BACKGROUND ART

As a conventional device that generates a mist used for sanitization, deodorization or the like, the mist-generating device disclosed in Patent Literature (PTL) 1 is known, for example. The mist-generating device according to PTL 1 generates a mist (floatable functional particles) by generating electrolyzed water containing a hydroxyl radical or hypochlorous acid having a disinfection effect by electrolysis of water, and atomizing the generated electrolyzed water by electrostatic atomization by applying a high voltage to the electrolyzed water with a discharging electrode.

Furthermore, there is a conventional technique of generating a droplet containing a plurality of materials (see PTL 2, for example).

The manufacturing device disclosed in PTL 2 has a nozzle including an outer tube and an inner tube that are concentrically formed, and first passes a first fluid material through the outer tube and then passes a second fluid material through the inner tube. After that, the manufacturing device disclosed in PTL 2 stops the flow of the second fluid material and then stops the flow of the first fluid material. By such a control, the manufacturing device disclosed in PTL 2 forms a droplet containing the first fluid material and the second fluid material covering the first fluid material.

It is possible to contemplate a method for extending the time for which a mist can dwell in the air, which uses a nozzle having an outer tube and an inner tube that are concentrically formed, such as the nozzle disclosed in PTL 2, to generate a mist formed by liquid droplets each containing a particle of a liquid and a different liquid covering the particle (such a mist or a liquid droplet forming the mist will be referred to as a multilayer mist, hereinafter).

Citation List

Patent Literature

PTL 1: Unexamined Patent Application Publication No. 2012-65979

PTL 2: Unexamined Patent Application Publication No. 2001-190943

SUMMARY OF THE INVENTION

TECHNICAL PROBLEMS

For example, with the mist-generating device disclosed in PTL 1, a fine mist having a diameter of the order of nanometers to micrometers can be generated. However, the mist of such a size immediately vaporizes while floating in the air. Therefore, the mist dwells in the air for a short time and can hardly travel far from the location where the mist is generated.

To generate a multilayer mist in the method disclosed in PTL 2, the flow rates of the two liquids ejected from the nozzle need to be extremely precisely controlled.

The present invention provides a mist-generating device capable of generating a multilayer mist, using a simple configuration.

SOLUTIONS TO PROBLEMS

A mist-generating device according to an aspect of the present invention includes: a droplet generating unit configured to generate, in a third liquid, a functional droplet including a first liquid that is spherical and a second liquid that covers an entirety of the first liquid and has a volatility lower than a volatility of the first liquid; and a mist-generating unit configured to generate a multilayer mist obtained by atomizing the third liquid containing the functional droplet.

ADVANTAGEOUS EFFECT OF INVENTION

The present invention can provide a mist-generating device capable of generating a multilayer mist, using a simple configuration.

DESCRIPTION OF EXEMPLARY EMBODIMENTS

Hereinafter, embodiments of the present invention will be described in detail with reference to the drawings. Note that each of the following embodiments shows a specific example of the present invention. Therefore, numerical values, shapes, materials, structural components, the arrangement and connection of the structural components, steps, the processing order of the steps, etc. shown in the following embodiments are mere examples, and thus are not intended to limit the present invention. Accordingly, among the structural components described in the following embodiments, structural components not recited in any one of the independent claims that indicate the broadest concepts of the present invention are described as optional structural components.

Furthermore, the respective figures are schematic diagrams and are not necessarily accurate illustrations. Therefore, for example, the scale, and so on, in the respective figures do not necessarily match. Furthermore, in the figures, elements which are substantially the same are given the same reference signs, and overlapping description is omitted or simplified.

In this specification, disinfection means destroying fungi such as *Staphylococcus aureus* or *Staphylococcus epidermidis*, bacteria such as *Escherichia coli, Pseudomonas* sp., or *Klebsiella* sp., Eumycetes including molds such as *Cladosporium* sp. or Aspergillus, and/or viruses such as norovirus and reducing the overall number thereof, and is also used as a synonym for sanitization or sterilization. The fungi, bacteria, Eumycetes, and viruses described above as targets to be killed are just examples, and the present invention is not limited thereto.

EMBODIMENT 1

[Configuration]

<Overview>

First, with reference to FIGS. 1 to 6, an overview of a configuration of a mist-generating device according to Embodiment 1 will be described.

Figure 1:
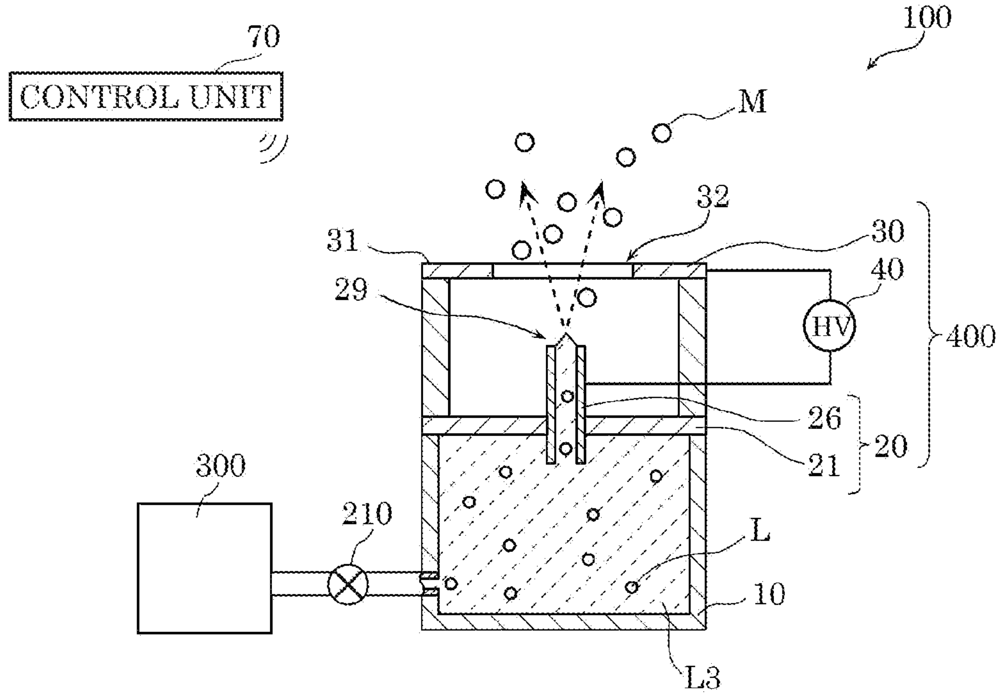
FIG. 1 is a cross-sectional view showing a configuration of a mist-generating device according to Embodiment 1.

FIG. 1 is a schematic cross-sectional view showing a configuration of mist-generating device 100 according to Embodiment 1. Note that FIG. 1 shows cross sections of some components, such as container 10 and ejection plate 20 and does not show cross sections of other components, such as droplet generating unit 300.

Mist-generating device 100 according to Embodiment 1 includes container 10, droplet generating unit 300, supplying unit 210, mist-generating unit 400, and control unit 70. Mist-generating unit 400 includes ejection plate 20, first electrode 30, and voltage applying unit 40. Ejection plate 20 includes electrode support plate 21 and nozzle 26.

FIG. 1 shows control unit 70 as a functional block. Control unit 70 is implemented by a microcomputer (microcontroller), for example, and is arranged inside an outer housing (not shown) of mist-generating device 100. Control unit 70 may be attached to the exterior of container 10, for example.

Mist-generating device 100 is a spray device that ejects multilayer mist M formed by atomizing third liquid L3 containing functional droplet L. For example, mist-generating device 100 is a device that generates multilayer mist M in an electrostatic atomization process, in which a high voltage is applied to third liquid L3 to produce an electrostatic force, which causes atomization of third liquid L3 containing functional droplet L. For example, when functional droplet L contains a disinfecting constituent or sanitizing constituent, such as hypochlorous acid or ozone, mist-generating device 100 is used as a disinfecting device or a sanitizing device, for example. Note that when functional droplet L contains an aromatic constituent, for example, mist-generating device 100 is used as an aroma generator that generates multilayer mist M containing an aromatic constituent.

In mist-generating device 100, supplying unit 210 supplies functional droplet L generated by droplet generating unit 300 to container 10, and mist-generating unit 400 atomizes third liquid L3 containing supplied functional droplet L and discharges the resulting mist. Note that third liquid L3 is a liquid that is highly volatile and will volatilize and disappear (or in other words turn into a gas) some time after the liquid is discharged into the air in small quantities.

Mist-generating unit 400 atomizes third liquid L3 containing functional droplet L. Mist-generating unit 400 introduces third liquid L3 containing functional droplet L to a tip end of nozzle 26 by the action of a pump (not shown) or the like, and ejects multilayer mist M, which is formed by atomizing third liquid L3, through opening 29 at the tip end of nozzle 26. In this embodiment, mist-generating unit 400 includes nozzle 26 for discharging third liquid L3 containing functional droplet L, and first electrode 30 that is arranged to be opposed to nozzle 26 and applies a voltage to third liquid L3 containing functional droplet L discharged from nozzle 26 to atomize third liquid L3 containing functional droplet L to generate multilayer mist M.

Specifically, in mist-generating unit 400, voltage applying unit 40 applies a high voltage between first electrode 30 and nozzle 26 to produce an electric field, and multilayer mist M is ejected from opening 29 of nozzle 26. Here, the "high voltage" is on the order of 5 kV with respect to a ground voltage (0 V), but is not particularly limited. Note that the voltage of first electrode 30 may be positive or negative with respect to the ground voltage.

A channel that introduces third liquid L3 containing functional droplet L to opening 29 in container 10 is formed in nozzle 26. Third liquid L3 containing functional droplet L having flowed in the channel and exited opening 29 is changed in shape by the electric field to form a Taylor cone. Third liquid L3 containing functional droplet L is atomized at the tip end of the Taylor cone to form multilayer mist M.

Note that, although FIG. 1 shows one nozzle 26, the number of nozzles 26 provided on ejection plate 20 is not particularly limited and may be two, or three or more.

Multilayer mist M generated at the tip end of nozzle 26 is discharged toward first electrode 30. In order to discharge multilayer mist M in the forward direction beyond first electrode 30, through-hole 32 is formed in flat plate part 31 of first electrode 30 at a position directly opposed to nozzle 26. This allows multilayer mist M to be discharged in the forward direction beyond first electrode 30. Here, the "forward direction" refers to a direction in which multilayer mist M is discharged and is the opposite direction to nozzle 26 with respect to first electrode 30.

Mist-generating unit 400 also charges third liquid L3 containing functional droplet L. In this embodiment, mist-generating unit 400 performs atomization and charging of third liquid L3 containing functional droplet L at the same time by atomizing third liquid L3 containing functional droplet L by electrostatic atomization.

Figure 2:
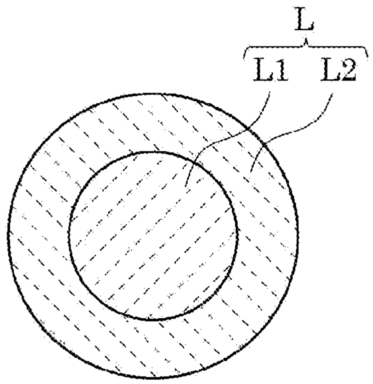
FIG. 2 is a cross-sectional view of a functional droplet generated by the mist-generating device according to Embodiment 1.

FIG. 2 is a cross-sectional view of functional droplet L generated by mist-generating device 100 according to Embodiment 1.

Functional droplet L is a liquid particle that has a predetermined function (effect). For example, functional droplet L is a liquid particle containing an aromatic constituent that has a function of generating an aroma when coming into contact with air, or a liquid particle that has a function of killing a target such as a fungus when coming into contact with the target.

Functional droplet L is formed by first liquid L1 having a granular (that is, spherical) shape, and second liquid L2 having a film-like shape that has a lower volatility than first liquid L1 and covers the whole of first liquid L1.

First liquid L1 is a liquid particle that has a predetermined function. For example, first liquid L1 is a liquid particle containing an aromatic constituent that has a function of generating an aroma when coming into contact with air, or a liquid particle that has a function of killing a target such as a fungus when coming into contact with the target. For example, when mist-generating device 100 is an aroma generator, first liquid L1 is an oily liquid containing an aromatic constituent. When mist-generating device 100 is a disinfecting device, for example, first liquid L1 is water containing a disinfection constituent, such as hypochlorous acid.

Second liquid L2 is a liquid that covers the whole of first liquid L1. For example, second liquid L2 is a liquid that has a lower volatility than first liquid L1. In other words, second liquid L2 is less susceptible to volatilization than first liquid L1, second liquid L2 serves to retard vaporization of first liquid L1 in the air. To this end, the volatility of second liquid L2 is lower than that of first liquid L1.

Second liquid L2 is formed to have a thickness that allows second liquid L2 to gradually volatilize or be lost until multilayer mist M reaches to a predetermined distance from the location where the mist is generated (that is, mist-generating device 100) so that first liquid L1 is exposed and comes into contact with air. Specifically, second liquid L2 is formed to have a thickness that allows second liquid L2 to volatilize or be lost to allow first liquid L1 to be exposed and come into contact with air when a predetermined time has elapsed or, in other words, when multilayer mist M generated by mist-generating device 100 has moved a predetermined distance. The predetermined distance can be arbitrarily determined. The thickness of second liquid L2 can be any thickness as far as second liquid L2 completely volatilizes when a predetermined time, which is arbitrarily determined in advance, has elapsed or, in other words, when multilayer mist M has moved the predetermined distance. For example, the thickness of second liquid L2 can be approximately equal to the radius of first liquid L1, greater than the radius of first liquid L1, or smaller than the radius of first liquid L1.

Alternatively, second liquid L2 may be a liquid that is nonvolatile or has extremely low volatility and have a structure that has a thickness that allows second liquid L2 to be broken when second liquid L2 comes into contact with an object while second liquid L2 is floating and moving in the air. In any case, multilayer mist M continues floating without delivering the function until multilayer mist M comes into contact with an object in the air, and gives the effect of first liquid L1 only after multilayer mist M comes into contact with an object in the air.

In order to prevent mixing of first liquid L1 and second liquid L2, for example, one of first liquid L1 and second liquid L2 is oily, and the other is aqueous. In addition, in order to prevent functional droplet L from being dissolved in third liquid L3 in container 10, one of second liquid L2 and third liquid L3 is oily, and the other is aqueous. That is, when first liquid L1 and third liquid L3 are aqueous, second liquid is oily, and when first liquid L1 and third liquid L3 are oily, second liquid L2 is aqueous.

When first liquid L1 is an oily liquid containing an aromatic constituent, for example, second liquid L2 is an aqueous liquid that has a lower volatility than first liquid L1. When first liquid L1 is water containing a disinfection constituent such as hypochlorous acid, for example, second liquid L2 is an oily liquid.

With such a configuration, first liquid L1 and second liquid L2 in functional droplet L are less likely to be mixed with each other. Therefore, with such a configuration, the floating time of multilayer mist M in the air can be extended.

Second liquid L2 is a biomaterial or a biocompatible material, for example. Here, the "biomaterial" refers to a liquid material present in the human body. The "biocompatible material" refers to a liquid material that is artificially produced and has a small influence on the human body when the material is taken in the human body. The biomaterial or biocompatible material is oleic acid, for example.

Note that oleic acid is oily. When second liquid L2 is aqueous, at least one of first liquid L1 and third liquid L3 may be oleic acid.

If a biomaterial or biocompatible material is used as an oily liquid for first liquid L1, second liquid L2, and third liquid L3, the possibility that multilayer mist M adversely affects the body of a user when the user inhales multilayer mist M can be reduced.

For example, third liquid L3 has a higher volatility than second liquid L2. For example, second liquid L2 has a lower volatility than first liquid L1.

Since third liquid L3 has a high volatility, third liquid L3 volatilizes in a short time while multilayer mist M is existing in the air. Since third liquid L3 volatilizes and thus is lost, multilayer mist M becomes lighter. Therefore, multilayer mist M can float for a longer time in the air. As an example, when first liquid L1 is water containing a low concentration of, such as 100 ppm or less of, hypochlorous acid, third liquid L3 is desirably formed by water containing hypochlorous acid as with first liquid L1. If first liquid L1 and third liquid L3 are the same kind of liquid, one supplying unit can be shared for replenishing (supplying) first liquid L1 and third liquid L3 to droplet generating unit 300, so that the structure of the device can be simplified. However, when first liquid L1 is an expensive liquid (such as an aroma oil), it is desirable that the device has separate supplying units for supplying first liquid L1 and third liquid L3 to nozzle 26, and an inexpensive liquid, which is different from first liquid L1, is used as third liquid L3 to reduce the cost of the liquid materials.

The outer diameter (particle diameter) of functional droplet L is equal to or smaller than 10 μm, for example.

With such a configuration, multilayer mist M does not fall under its own weight in a short time, and can float in the air for an elongated time.

The particle diameter of functional droplet L may be equal to or smaller than 5 μm. The particle diameter of functional droplet L may also be equal to or greater than 10 nm and equal to or smaller than 3 μm.

The volume of second liquid L2 in functional droplet L contained in multilayer mist M is preferably small enough not to adversely affect the user who inhales or otherwise takes in multilayer mist M.

As disclosed on the webpage of International Pharmaceutical Excipients Council Japan (URL: http://www.jpec.gr.jp/document/safety.html), the maximum dose per day of oleic acid as an inhalant is 0.1668 mg. Therefore, by setting the thickness of second liquid L2 so that the amount of inhalation is equal to or smaller than 0.1688 mg, the safety of the living human body can be assured even if multilayer mist M containing oleic acid as second liquid L2 is sprayed into the space in which the human body is present. For example, when second liquid L2 is oleic acid, which is oily, the particle diameter of functional droplet L is 5 μm, and mist-generating device 100 sprays multilayer mist M into a space having a volume of 20 $m^3$ at a rate of 0.1 mL/h for up to six hours per day, the thickness of second liquid L2 in functional droplet L is on the order of 10 nm. In this way, multilayer mist M can be prevented from adversely affecting the human body. The thickness of second liquid L2 in functional droplet L is controlled by adjusting the size or shape of droplet generating units 300, 300*a*, and 300*b* described later and the flowrate or the like of first liquid L1, second liquid L2, and third liquid L3 flowing in the channels of droplet generating units 300, 300*a*, and 300*b* described later.

Figure 3:
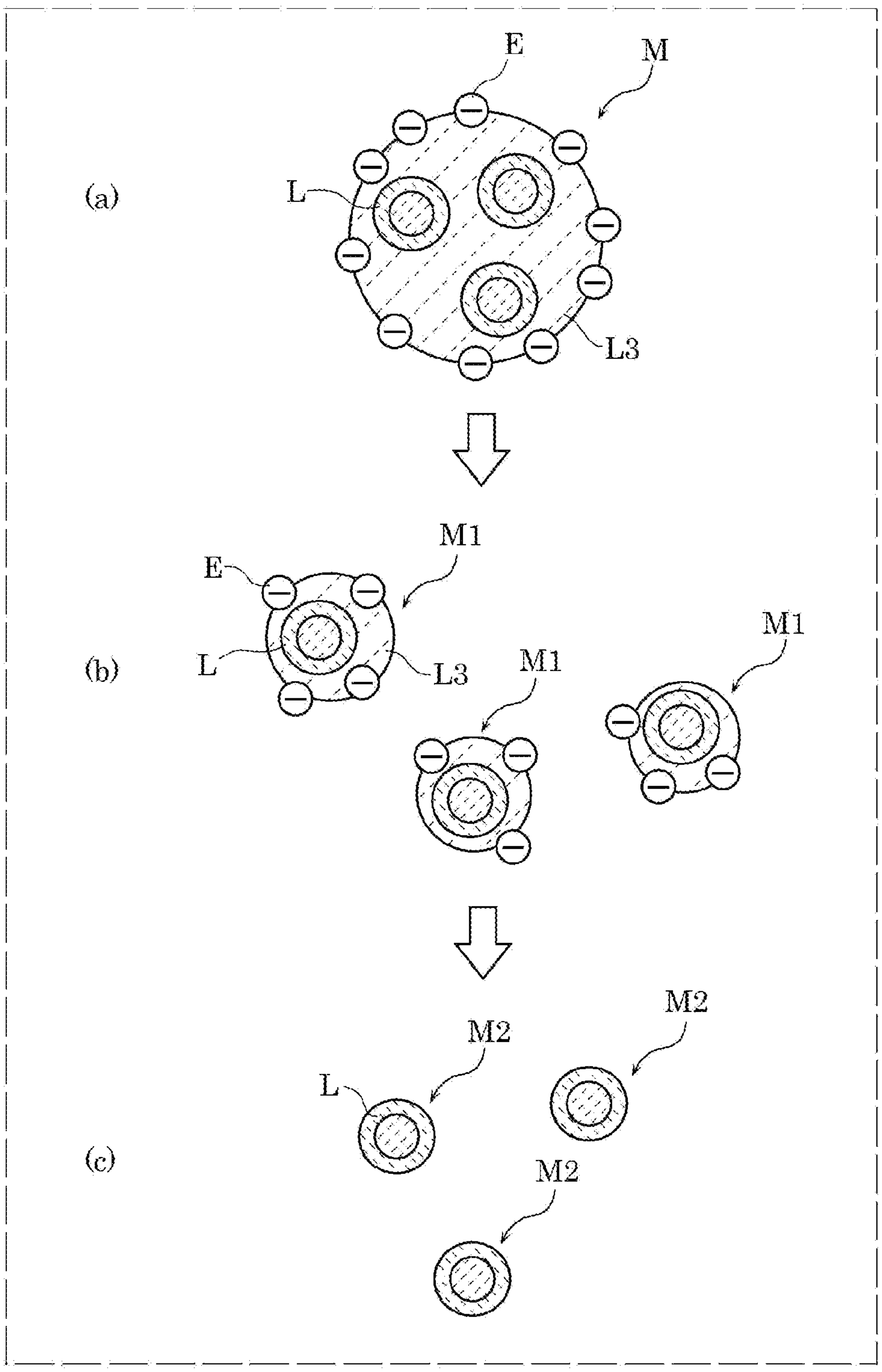
FIG. 3 is a schematic diagram showing fission of a multilayer mist generated by the mist-generating device according to Embodiment 1.

FIG. 3 is a schematic diagram showing fission of multilayer mist M generated by mist-generating device 100 according to Embodiment 1.

Multilayer mist M is an aggregate of liquid particles of third liquid L3 containing one or more functional droplet L. Multilayer mist M is an aggregate of fine liquid particles having a diameter of 100 μm or less.

As shown in part (a) of FIG. 3, multilayer mist M is electrostatically atomized and discharged from nozzle 26 shown in FIG. 1 in the form of a droplet containing functional droplet L and electric charge E.

Note that, although part (a) of FIG. 3 shows a case where three functional droplets L are contained as an example, multilayer mist M can contain any number of functional droplets L. Although parts (a) and (b) of FIG. 3 show a case where electric charge E is negative as an example, electric charge E may be positive. The polarity of electric charge E depends on whether the voltage applied to first electrode 30 is positive or negative.

As shown in part (b) of FIG. 3, electric charge E then causes a Rayleigh fission of multilayer mist M shown in part (a) of FIG. 3, and multilayer mist M splits into a plurality of multilayer mists M1.

As shown in part (c) of FIG. 3, third liquid L3 in multilayer mist M1 shown in part (b) of FIG. 3 then volatilizes, and a plurality of multilayer mists M2 having functional droplet L exposed to the air is thus generated.

Multilayer mist M discharged from nozzle 26 has a particle diameter of the order of several tens of μm immediately after multilayer mist M is discharged. However, multilayer mist M immediately splits, and third liquid L3 volatilizes. In this way, multilayer mist M2 is formed which is formed by functional droplet L alone and has a particle diameter of 10 μm or less. To this end, third liquid L3 has a volatility. Third liquid L3 preferably volatilizes in a short time in the air. For example, third liquid L3 has a higher volatility than second liquid L2. For example, third liquid L3 also has a higher volatility than first liquid L1.

In the following description, multilayer mist M will be basically described as multilayer mist M containing first liquid L1 having the shape of a spherical core and second liquid L2 covering the entire surface of first liquid L1. However, the present invention is not limited thereto. For example, multilayer mist M may be discharged into the air by atomizing third liquid L3 containing multilayer functional droplet L formed by second liquid L2 the entire surface of which is covered by a fourth liquid (not shown) the entire surface of which is covered by a fifth liquid (not shown), which is different from the fourth liquid. In that case, if first liquid L1 is oily, second liquid L2, which forms a layer adjacent first liquid L1, is desirably aqueous in order to prevent mixing thereof. Similarly, the fourth liquid (not shown), which forms a layer adjacent to second liquid L2, is desirably oily in order to prevent mixing thereof, and third liquid L3 is desirably aqueous. On the other hand, if first liquid L1 is aqueous, second liquid L2, which forms a layer adjacent first liquid L1, is desirably oily in order to prevent mixing thereof. Similarly, the fourth liquid (not shown), which forms a layer adjacent to second liquid L2, is desirably aqueous in order to prevent mixing thereof, and third liquid L3 is desirably oily. As described above, as far as a predetermined weight is not exceeded, this concept can be extended to n layers (n represents a natural number). This concept is independent from whether the mist has electric charge E or not.

In the following, each component of mist-generating device 100 will be described in detail.

<Container>

Container 10 is a container that accommodates third liquid L3. When second liquid L2 is an oily liquid, for example, third liquid L3 is an aqueous liquid. When second liquid L2 is water containing a disinfection constituent such as hypochlorous acid, for example, third liquid L3 is an oily liquid.

Container 10 is made of a metal material such as stainless steel, for example. However, container 10 may be made of a resin material. Container 10 may be made of a material having one or both of acid resistance and alkali resistance.

Container 10 has the shape of a cylinder with an open top, for example. However, the shape of container 10 is not limited thereto. Container 10 may have the shape of a cube, a rectangular parallelepiped, or a flat tray. The open top of container 10 is covered by ejection plate 20.

<Ejection Plate>

Ejection plate 20 has opening 29 through which third liquid L3 containing functional droplet L is ejected. Specifically, ejection plate 20 includes electrode support plate 21 having a planar shape, and nozzle 26. Opening 29 is formed at a tip end of nozzle 26.

Electrode support plate 21 is a plate-like member that supports nozzle 26. Electrode support plate 21 is made of a resin material, for example. However, electrode support plate 21 may be made of a metal material. Electrode support plate 21 may be made of a material having one or both of acid resistance and alkali resistance.

Nozzle 26 is fixed to electrode support plate 21 by press-fitting. For example, a through-hole is formed in electrode support plate 21 at a location where opening 29 is to be provided, and nozzle 26 is inserted into the through-hole and fixed. Electrode support plate 21 is a flat plate having a uniform thickness. However, the present invention is not thereto, and electrode support plate 21 may be a curved plate.

Electrode support plate 21 is fixed to container 10. Electrode support plate 21 may be made of the same material as container 10 and formed integrally with container 10.

Nozzle 26 is a nozzle for discharging third liquid L3 containing functional droplet L to the outside of container 10. Specifically, nozzle 26 is supported by electrode support plate 21, and discharges third liquid L3 containing functional droplet L in container 10 to the outside of container 10. Nozzle 26 projects toward first electrode 30 from electrode support plate 21. Nozzle 26 has opening 29 at a tip end thereof. Nozzle 26 also has an opening at a rear end thereof (that is, an end on the side of container 10), and a channel extending from the opening to opening 29.

Nozzle 26 has the shape of a cylinder having uniform inner and outer diameters, for example. The inner diameter is the diameter of the channel, and is 0.3 mm, for example. However, the present invention is not limited thereto. The outer diameter is 0.5 mm, for example. However, the present invention is not limited thereto. For example, the outer diameter may fall within a range from 0.5 mm to 1.5 mm inclusive. The channel formed in nozzle 26 has the shape of a cylinder having a uniform cross-sectional area, for example.

Note that at least one of the inner and outer diameters of nozzle 26 may be tapered from the rear end toward the tip end. For example, the opening at the rear end may be smaller than opening 29 at the tip end, and the channel connecting these openings may have the shape of a truncated cone.

The rear end of nozzle 26 is positioned at a location where the rear end is in contact with third liquid L3 in container 10. Specifically, the rear end of nozzle 26 is located inside container 10. This allows third liquid L3 to be introduced from the opening at the rear end of nozzle 26 to opening 29 at the tip end thereof through the channel in nozzle 26.

Nozzle 26 stands perpendicularly to a principal surface (specifically, a surface closer to first electrode 30) of electrode support plate 21. The principal surface is a surface of electrode support plate 21 that is opposed to first electrode 30 and is on the opposite side to container 10. The ratio of height to outer diameter (referred to as an aspect ratio, hereinafter) of nozzle 26 is preferably equal to or greater than 4. The height of nozzle 26 is represented by the distance from the tip end of nozzle 26 to the principal surface. The height is equal to or greater than 2 mm, for example. The greater the aspect ratio of nozzle 26, the more easily the electric field is concentrated at the tip end of nozzle 26. Therefore, the aspect ratio of nozzle 26 can be equal to or greater than 6, for example.

The material of nozzle 26 is not particularly limited. For example, nozzle 26 may be a metal material having a conductivity, such as stainless steel. Nozzle 26 may be made of a material having one or both of acid resistance and alkali resistance. Nozzle 26 may be made of a material having insulation properties, such as resin.

For example, if nozzle 26 is made of a conductive material, nozzle 26 can serve as an electrode (second electrode) paired with first electrode 30. In this embodiment, nozzle 26 is paired with first electrode 30, and a voltage is applied to third liquid L3 discharged from nozzle 26 to produce multilayer mist M.

Note that mist-generating device 100 may be provided with an electrode housed in container 10, as a second electrode paired with first electrode 30, for example. In that case, voltage applying unit 40 is electrically connected to first electrode 30 and the second electrode. In that case, nozzle 26 may be made of a material having insulation properties, such as resin.

Although FIG. 1 shows one nozzle 26, the number of nozzles 26 provided on ejection plate 20 is not particularly limited, and two, or three or more nozzles 26 may be provided. In that case, through-hole 32 is preferably formed in first electrode 30 at a location directly opposed to each of the plurality of nozzles 26.

<First Electrode>

First electrode is an opposed electrode that is arranged outside container 10 in such a manner that through-hole 32 is opposed to opening 29. Specifically, first electrode 30 is arranged outside container 10 to be opposed to nozzle 26 paired with first electrode 30. When a voltage is applied between first electrode 30 and nozzle 26, third liquid L3 containing functional droplet L discharged from the tip end of nozzle 26 is atomized. First electrode 30 is arranged in parallel with electrode support plate 21 of ejection plate 20, for example. Specifically, a rear surface of first electrode 30 is in parallel with the principal surface of electrode support plate 21.

First electrode 30 is made of a metal material having a conductivity, such as stainless steel. First electrode 30 may be made of a material having one or both of acid resistance and alkali resistance.

First electrode 30 includes flat plate part 31 and through-hole 32. Flat plate part 31 is conductive and is electrically connected to voltage applying unit 40. Flat plate part 31 has a substantially uniform thickness. Nozzle 26 is also conductive and is electrically connected to voltage applying unit 40.

Through-hole 32 passes through flat plate part 31 in the thickness direction (that is, the back-and-forth direction). Through-hole 32 is provided to allow atomized third liquid L3 containing functional droplet L ejected from opening 29, that is, multilayer mist M, to pass through flat plate part 31. Through-hole 32 has a flat cylindrical shape. The shape of the opening of through-hole 32 is not limited to a circle but can be a square, a rectangle, or an ellipse, for example.

The diameter of the opening of through-hole 32 is not particularly limited. For example, the diameter falls within a range from 1 mm to 2.25 mm inclusive. The diameter of the opening of through-hole 32 may be five or more times greater than and ten or less times smaller than the outer diameter of nozzle 26. Multilayer mist M discharged from the tip end of the Taylor cone spreads in a conical shape. Therefore, the greater the diameter of the opening of through-hole 32, the more multilayer mist M passes through through-hole 32.

<Voltage Applying Unit>

Voltage applying unit 40 applies a predetermined voltage between third liquid L3 and first electrode 30. Specifically, voltage applying unit 40 is connected to first electrode 30 and nozzle 26, and applies a voltage so as to produce a predetermined potential difference between first electrode 30 and nozzle 26. For example, nozzle 26 is grounded, and third liquid L3 is at the ground potential. Voltage applying unit 40 applies a potential to first electrode 30, thereby applying a predetermined voltage between first electrode 30 and third liquid L3. Note that voltage applying unit 40 may apply a positive voltage to first electrode 30 or apply a negative voltage to first electrode 30.

The predetermined voltage applied by voltage applying unit 40 is a direct-current voltage equal to or higher than 3.5 kV and equal to or lower than 10 kV. Alternatively, the predetermined voltage may be equal to or higher than 4.5 kV and equal to or lower than 8.5 kV. Note that the predetermined voltage may be a pulse voltage, a pulsating voltage, or an alternating-current voltage.

Specifically, voltage applying unit 40 is implemented by a power supply circuit including a converter or the like. For example, voltage applying unit 40 applies a voltage to third liquid L3 by generating a predetermined voltage based on an electric power received from an external power supply, such as a utility power supply, and applying the generated voltage between first electrode 30 and nozzle 26.

<Supplying Unit>

Supplying unit 210 supplies functional droplet L generated by droplet generating unit 300 into third liquid L3 in container 10. Supplying unit 210 supplies third liquid L3 containing functional droplet L generated by droplet generating unit 300 to mist-generating unit 400. Supplying unit 210 is a pump, for example. Supplying unit 210 supplies functional droplet L from droplet generating unit 300 into third liquid L3 in container 10 through piping connecting droplet generating unit 300 to the interior of container 10. Note that supplying unit 210 has only to supply functional droplet L to container 10 and may be provided with a solenoid valve or the like.

<Control Unit>

Control unit 70 is a controlling device that controls the overall operation of mist-generating device 100. Specifically, control unit 70 controls operations of voltage applying unit 40 and supplying unit 210. For example, control unit 70 controls voltage applying unit 40, thereby controlling the timing of application of a voltage between first electrode 30 and nozzle 26 and the magnitude of the voltage, for example.

Control unit 70 is implemented by a microcontroller, for example. Specifically, control unit 70 is implemented by a nonvolatile memory storing a program, a volatile memory used as a temporary storage area for execution of the program, an input/output port, a processor that executes the program, and the like. Control unit 70 may be implemented by a dedicated electronic circuit that realizes each operation.

Note that control unit 70 has only to be able to control voltage applying unit 40 and supplying unit 210, and may control voltage applying unit 40 and supplying unit 210 by transmitting a radio signal or may be connected to voltage applying unit 40 and supplying unit 210 by a control line or the like.

<Droplet generating unit>

Next, with reference to FIGS. 4 to 6, a specific configuration of the droplet generating unit of mist-generating device 100 according to Embodiment 1 will be described.

Figure 4:
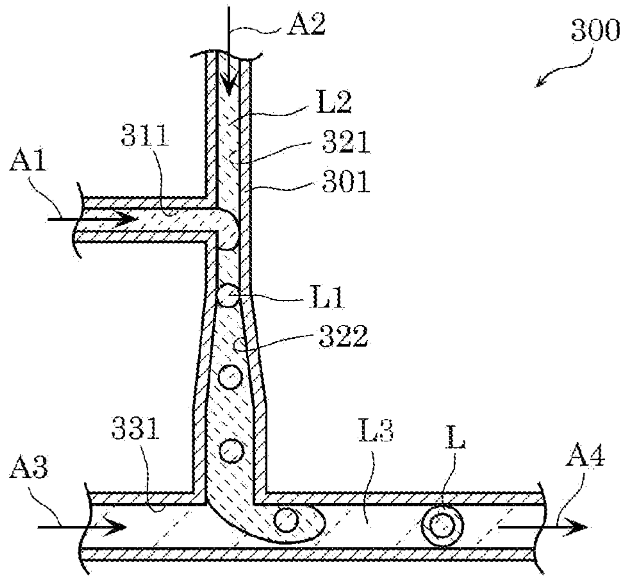
FIG. 4 is a schematic diagram showing a first example of the droplet generating unit of the mist-generating device according to Embodiment 1.
Figure 5:
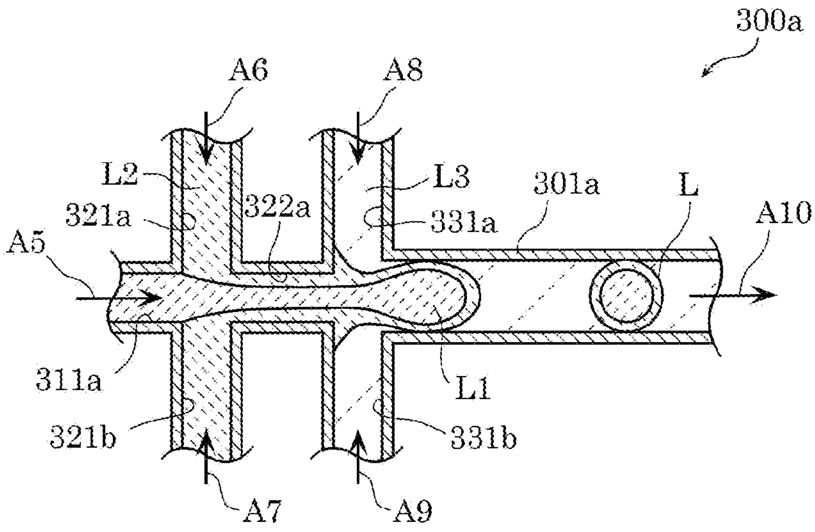
FIG. 5 is a schematic diagram showing a second example of the droplet generating unit of the mist-generating device according to Embodiment 1.
Figure 6:
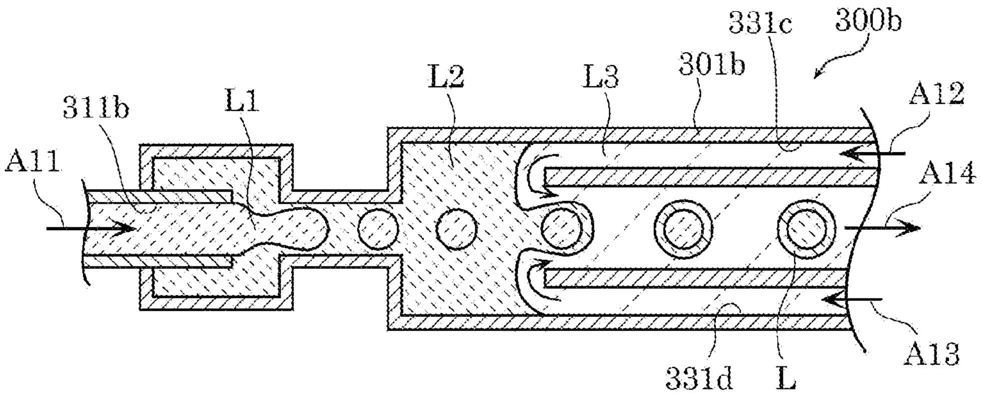
FIG. 6 is a schematic diagram showing a third example of the droplet generating unit of the mist-generating device according to Embodiment 1.

Note that FIGS. 4 to 6 are enlarged views of a part of the droplet generating unit that generates functional droplet L, in which illustration of the supplying unit that supplies first liquid L1, second liquid L2, and third liquid L3 to the part that generates functional droplet L is omitted. In FIGS. 4 and 5, each component is indicated by hatched lines, although the hatched lines do not represent the cross section of the component.

FIG. 4 is a schematic diagram showing a first example of the droplet generating unit of mist-generating device 100 according to Embodiment 1.

The droplet generating unit of mist-generating device 100 is a device that generates functional droplet L in third liquid L3, functional droplet L containing first liquid L1 that has a spherical shape and second liquid L2 that has a lower volatility than first liquid L1 and covers the whole of first liquid L1.

Droplet generating unit 300 in the first example includes microchannel chip 301, which is a microfluidic device that has a channel having a size of the order of micrometers, and a supplying unit (not shown) that supplies first liquid L1, second liquid L2, and third liquid L3 to microchannel chip 301. FIG. 4 is a partial enlarged view of microchannel chip 301.

Microchannel chip 301 is a plate-like body in which a channel is formed through which first liquid L1, second liquid L2, and third liquid L3 pass. The channel of microchannel chip 301 branches in a T-shaped, X-shaped, and/or Y-shaped configuration. In this embodiment, microchannel chip 301 has first liquid channel 311 through which first liquid L1 passes, second liquid channel 321 through which second liquid L2 passes, mixing channel 322 that is connected to first liquid channel 311 and second liquid channel 321 and allows the whole of first liquid L1 to be covered by second liquid L2, and third liquid channel 331 that is connected to mixing channel 322 and allows the whole of first liquid L1 and second liquid L2 to be covered by third liquid L3.

Microchannel chip 301 is made of a glass material, a resin material, or an inorganic material such as metal or silicon, for example.

For example, first liquid L1 is introduced to first liquid channel 311. Specifically, first liquid L1 is introduced into microchannel chip 301 in the direction indicated by arrow A1.

Second liquid L2 is introduced to second liquid channel 321. Specifically, second liquid L2 is introduced into microchannel chip 301 in the direction indicated by arrow A2. The direction of arrow A1, which is the direction in which first liquid L1 moves, is perpendicular to the direction of arrow A2, which is the direction in which second liquid L2 moves. Therefore, by appropriately adjusting the amounts of first liquid L1 and second liquid L2 flowing into microchannel chip 301, first liquid L1 is divided into spherical liquid particles. In this way, at the intersection (point of connection) between first liquid channel 311 and second liquid channel 321, second liquid L2 covers first liquid L1 so as to form first liquid L1 into spherical particles, and flows through mixing channel 322.

Third liquid L3 is introduced to third liquid channel 331. Specifically, third liquid L3 is introduced into microchannel chip 301 in the direction indicated by arrow A3. The direction of arrow A2, which is the direction in which second liquid L2 and spherical particles of first liquid L1 move, is perpendicular to the direction of arrow A3, which is the direction in which third liquid L3 moves. Therefore, by appropriately adjusting the amounts of second liquid L2 and third liquid L3 flowing into microchannel chip 301, second liquid L2 is divided into spherical liquid particles containing spherical particles of first liquid L1. The spherical particles of second liquid L2 containing spherical particles of first liquid L1 thus formed are functional droplets L. In other words, at the intersection (point of connection) between mixing channel 322 and third liquid channel 331, third liquid L3 covers second liquid L2 so as to form second liquid L2 covering first liquid L1 into spherical particles. In this way, functional droplet L covered by third liquid L3 is generated in microchannel chip 301.

Functional droplet L moves in the direction indicated by arrow A4, and is supplied into third liquid L3 in container 10 by supplying unit 210, for example.

As described above, the first example of droplet generating unit 300 is microchannel chip 301 that has first liquid channel 311 through which first liquid L1 passes, second liquid channel 321 through which second liquid L2 passes, mixing channel 322 that is connected to first liquid channel 311 and second liquid channel 321 and allows the whole of first liquid L1 to be covered by second liquid L2, and third liquid channel 331 that is connected to mixing channel 322 and allows the whole of first liquid L1 and second liquid L2 to be covered by third liquid L3.

With such a configuration, functional droplet L contained in third liquid L3 can be generated with a simple configuration.

FIG. 5 is a schematic diagram showing a second example of the droplet generating unit of mist-generating device 100 according to Embodiment 1.

Droplet generating unit 300*a* includes microchannel chip 301*a*, and a supplying unit (not shown) that supplies first liquid L1, second liquid L2, and third liquid L3 to microchannel chip 301*a*. FIG. 5 is a partial enlarged view of microchannel chip 301*a*.

Microchannel chip 301*a* is a plate-like body in which channels are formed through which first liquid L1, second liquid L2, and third liquid L3 pass. Microchannel chip 301*a* is made of a glass material or a resin material, for example.

First liquid L1 is introduced to first liquid channel 311*a* in microchannel chip 301*a* in the direction indicated by arrow A5.

Second liquid L2 is introduced to second liquid channel 321*a* in microchannel chip 301*a* in the direction indicated by arrow A6. Second liquid L2 is also introduced to second liquid channel 321*b* in microchannel chip 301*a* in the direction indicated by arrow A7. Arrows A6 and A7 are straight, are in parallel with each other, and indicate the opposite directions, for example.

In this way, second liquid L2 is positioned in mixing channel 322*a* in microchannel chip 301*a* to cover first liquid L1.

Third liquid L3 is introduced to third liquid channel 331*a* in microchannel chip 301*a* in the direction indicated by arrow A8.

Third liquid L3 is also introduced to third liquid channel 331*b* in microchannel chip 301*a* in the direction indicated by arrow A9. Arrows A8 and A9 are straight, are in parallel with each other, and indicate the opposite directions, for example.

In this way, third liquid L3 divides first liquid L1 and second liquid L2 covering first liquid L1 into spherical functional droplets L.

Functional droplet L moves in the direction indicated by arrow A10, and is supplied into third liquid L3 in container 10 by supplying unit 210, for example.

FIG. 6 is a schematic diagram showing a third example of the droplet generating unit of mist-generating device 100 according to Embodiment 1.

Droplet generating unit 300*b* includes complex nozzle 301*b*, and a supplying unit (not shown) that supplies first liquid L1, second liquid L2, and third liquid L3 to complex nozzle 301*b*. FIG. 6 is a partial enlarged cross-sectional view of complex nozzle 301*b*.

Complex nozzle 301*b* is a cylindrical nozzle in which channels are formed through which first liquid L1, second liquid L2, and third liquid L3 pass. Complex nozzle 301*b* is made of a metal material, a glass material, or a resin material, for example.

Complex nozzle 301*b* includes a nozzle to which first liquid L1 is introduced, a nozzle for ejecting functional droplet L generated in complex nozzle 301*b*, and a nozzle that covers and connects these nozzles.

First liquid L1 is introduced from first liquid channel 311*b* into complex nozzle 301*b* in the direction indicated by arrow A11.

Second liquid L2 is contained in advance in complex nozzle 301*b*.

When an appropriate amount of first liquid L1 is introduced from first liquid channel 311*b* into complex nozzle 301*b* in the direction indicated by arrow A11, first liquid L1 is divided into spherical liquid particles, which are covered by second liquid L2.

Third liquid L3 is introduced from third liquid channels 331*c* and 331*d* in complex nozzle 301*b* in the directions indicated by arrows A12 and A13, which are in parallel with and indicate the opposite directions to arrow A14, which indicates the direction in which functional droplet L is ejected.

With such a configuration, third liquid L3 divides second liquid L2 covering first liquid L1 into spherical functional droplets L, moves along with functional droplets L in the direction indicated by arrow A14, and is supplied into third liquid L3 in container 10 by supplying unit 210, for example.

Note that first liquid channel 311, second liquid channel 321, mixing channel 322, and third liquid channel 331 in microchannel chip 301 may have different wettabilities depending on whether first liquid L1, second liquid L2, and third liquid L3 are aqueous or oily.

For example, when first liquid L1 is aqueous, first liquid channel 311 through which first liquid L1 passes has a higher wettability to water (water phase) than to oil (oil phase).

For example, when second liquid L2 is oily, second liquid channel 321 through which second liquid L2 passes and mixing channel 322 have a higher wettability to oil than to water.

For example, when third liquid L3 is aqueous, third liquid channel 331 through which third liquid L3 passes has a higher wettability to water than to oil.

With such a configuration, first liquid L1, second liquid L2, and third liquid L3 can more easily flow in the channels through which first liquid L1, second liquid L2, and third liquid L3 pass. With such a configuration, in addition, for example, second liquid L2 can more easily cover first liquid L1 so as to form first liquid L1 into spherical particles at the intersection between first liquid channel 311 and second liquid channel 321. With such a configuration, in addition, third liquid L3 can more easily cover second liquid L2 so as to form second liquid L2 covering first liquid L1 into spherical particles at the intersection (point of connection) between mixing channel 322 and third liquid channel 331.

Note that the wettability of the channels is adjusted by changing the material of microchannel chip 301 or modifying the shapes of the inner surfaces of the channels, for example. Although microchannel chip 301 shown in FIG. 4 is constituted by one microchannel chip, microchannel chip 301 may be a combination of a plurality of microchannel chips having channels having different wettabilities.

The above description of the wettability of the channels applies to the wettability of the channels of droplet generating units 300*a* and 300*b*.

[Operation]

Figure 7:
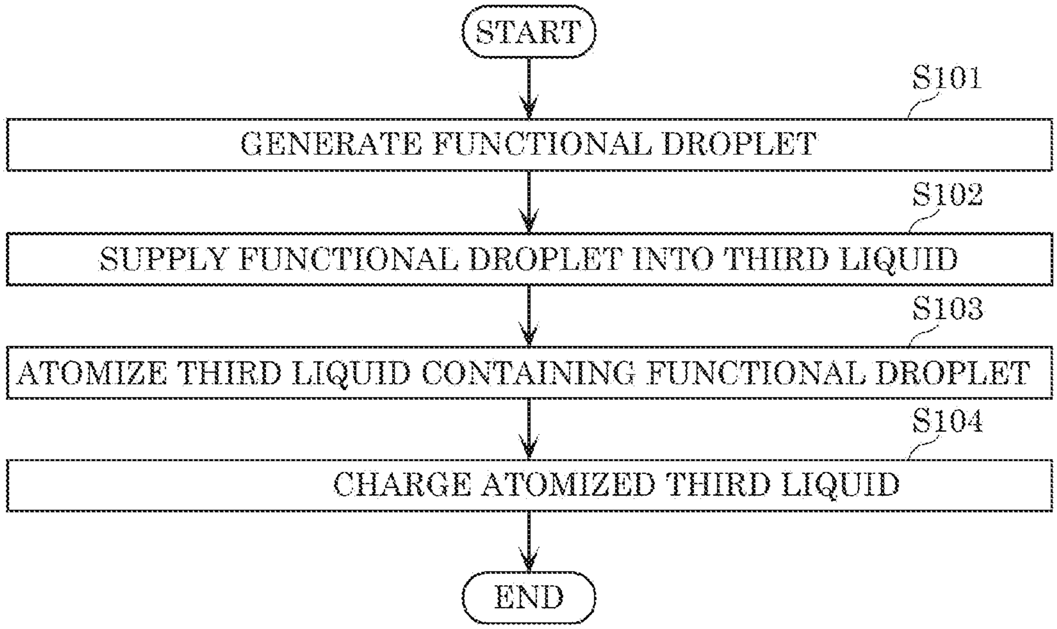
FIG. 7 is a flowchart showing an operation procedure of the mist-generating device according to Embodiment 1.

Next, with reference to FIG. 7, an operation of mist-generating device 100 according to Embodiment 1 will be described.

First, droplet generating unit 300 performs a first step of generating functional droplet L (step S101).

Supplying unit 210 then performs a second step of supplying functional droplet L generated by droplet generating unit 300 into third liquid L3 in container 10 (step S102).

Mist-generating unit 400 then performs a third step of atomizing third liquid L3 containing functional droplet L (step S103).

Mist-generating unit 400 also performs a fourth step of charging atomized third liquid L3 containing functional droplet L (step S104). Note that, in this embodiment, mist-generating unit 400 atomizes third liquid L3 containing functional droplet L in an electrostatic atomization process, so that mist-generating unit 400 charges third liquid L3 while atomizing third liquid L3. That is, in this embodiment, steps S103 and S104 are performed at the same time in the electrostatic atomization process performed by mist-generating unit 400.

[Effects and the like]

As described above, the mist-generating method according to Embodiment 1 includes a first step of generating functional droplet L that contains first liquid L1 that has a spherical shape and second liquid L2 that has a lower volatility than first liquid L1 and covers the whole of first liquid L1, a second step of supplying functional droplet L into third liquid L3, and a third step of atomizing third liquid L3 containing functional droplet L.

According to such a method, as with the method according to the related art for covering an atomized liquid with a different liquid when atomizing a liquid, functional droplet L containing first liquid L1 covered by second liquid L2 can be atomized. According to the mist-generating method according to Embodiment 1, the flowrate of the liquid discharged from the nozzle does not have to be precisely controlled unlike the related art, and therefore, multilayer mist M can be generated more simply than conventional.

For example, the mist-generating method according to Embodiment 1 further includes a fourth step of charging third liquid L3 containing functional droplet L.

According to such a method, multilayer mist M splits into a plurality of multilayer mists M1 by Rayleigh fission. Third liquid L3 of the plurality of multilayer mists M1 resulting from the fission of multilayer mist M has a greater area of contact with air than third liquid L3 of multilayer mist M yet to split. Therefore, third liquid L3 of the plurality of multilayer mists M1 resulting from the fission of multilayer mist M more easily vaporizes than third liquid L3 of multilayer mist M yet to split. Therefore, multilayer mists M2, which are formed by functional droplets L and do not contain third liquid L3, can be more quickly discharged into the air.

For example, in the mist-generating method according to Embodiment 1, the third step and the fourth step described above are performed at the same time by atomizing third liquid L3 containing functional droplet L in the electrostatic atomization process.

According to such a method, atomization and charging of third liquid L3 containing functional droplet L can be performed at the same time by mist-generating unit 400. Therefore, according to such a method, third liquid L3 containing functional droplet L can be simply charged.

For example, third liquid L3 has a higher volatility than second liquid L2.

Therefore, third liquid L3 contained in multilayer mist M immediately volatilizes. Therefore, according to such a method, multilayer mist M2, which is formed by functional droplet L and does not contain third liquid L3, can be immediately discharged into the air.

Mist-generating device 100 according to Embodiment 1 includes droplet generating unit 300 that generates functional droplet L in third liquid L3, functional droplet L containing first liquid L1 that has a spherical shape and second liquid L2 that has a lower volatility than first liquid L1 and covers the whole of first liquid L1, and mist-generating unit 400 that atomizes third liquid L3 containing functional droplet L. In this embodiment, mist-generating device 100 further includes supplying unit 210 that supplies third liquid L3 containing functional droplet L generated by droplet generating unit 300 to mist-generating unit 400.

With such a configuration, without the need of the precise control for covering an atomized liquid with a different liquid when atomizing a liquid through a nozzle according to the related art, functional droplet L containing first liquid L1 covered by second liquid L2 can be atomized. With mist-generating device 100, multilayer mist M can be more simply generated than conventional.

Since mist-generating device 100 includes supplying unit 210, droplet generating unit 300 and mist-generating unit 400 can be arranged at a distance. Therefore, the convenience of mist-generating device 100 can be improved.

(Variation 1)

Figure 8:
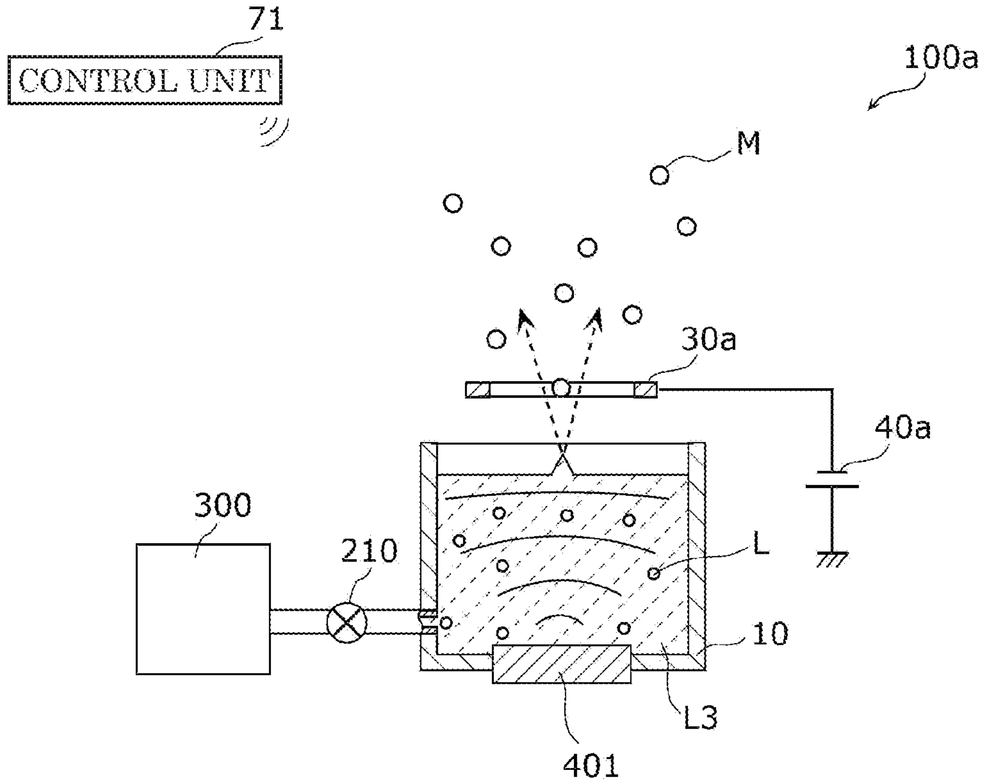
FIG. 8 is a cross-sectional view showing a configuration of a mist-generating device according to Variation 1 of Embodiment 1.

FIG. 8 is a cross-sectional view showing a configuration of mist-generating device 100*a* according to Variation 1 of Embodiment 1.

Note that the components of mist-generating device 100*a* according to Variation 1 of Embodiment 1 that are substantially the same as those of mist-generating device 100 according to Embodiment 1 are denoted by the same reference numerals, and descriptions thereof will be simplified or omitted.

Mist-generating device 100*a* according to Variation 1 of Embodiment 1 differs from mist-generating device 100 according to Embodiment 1 in that third liquid L3 is atomized by ultrasonic vibration.

Mist-generating device 100*a* includes container 10, supplying unit 210, droplet generating unit 300, mist-generating unit 401, charging electrode 30*a*, voltage applying unit 40*a*, and control unit 71.

Mist-generating unit 401 is an ultrasonic generating device that applies an ultrasonic vibration to third liquid L3 containing functional droplet L in container 10. Mist-generating unit 401 is arranged at a location where mist-generating unit 401 is in contact with third liquid L3 in container 10, for example. Mist-generating unit 401 is an ultrasonic transducer, for example. Note that mist-generating unit 401 has only to be able to apply an ultrasonic vibration to third liquid L3 in container 10, and may be arranged outside container 10 and apply an ultrasonic vibration to third liquid L3 in container 10 by applying the ultrasonic vibration to container 10.

Charging electrode 30*a* is an electrode for charging multilayer mist M. Charging electrode 30*a* is a ring electrode having an annular shape, for example, and generates multilayer mist M having electric charge E by charging multilayer mist M passing through the inner space of the ring electrode.

As described above, mist-generating device 100*a* includes mist-generating unit 401 that generates multilayer mist M, and a charging unit that has charging electrode 30*a* that charges multilayer mist M. Mist-generating device 100*a* generates multilayer mist M having electric charge E by atomizing third liquid L3 containing functional droplet L to generate multilayer mist M having no electric charge E and then charging multilayer mist M with charging electrode 30*a*.

Voltage applying unit 40*a* is connected to charging electrode 30*a*, and applies a predetermined voltage to charging electrode 30*a*. Voltage applying unit 40*a* charges multilayer mist M passing through the periphery of charging electrode 30*a* by applying a potential to charging electrode 30*a*. Note that, although voltage applying unit 40*a* applies a negative voltage to charging electrode 30*a* in FIG. 8, voltage applying unit 40*a* may apply a positive voltage to charging electrode 30*a*.

Note that the predetermined voltage applied by voltage applying unit 40*a* may be a pulse voltage, a pulsating voltage, or an alternating-current voltage.

Voltage applying unit 40*a* is implemented by a power supply circuit including a converter or the like, for example. For example, voltage applying unit 40*a* generates a predetermined voltage based on an electric power received from an external power supply, such as a utility power supply, and applies the generated voltage to charging electrode 30*a*.

Control unit 71 is a controlling device that controls the overall operation of mist-generating device 100*a*. Specifically, control unit 71 controls operations of voltage applying unit 40*a*, supplying unit 210, and mist-generating unit 401. For example, control unit 71 controls mist-generating unit 401, thereby controlling the timing of generation of multilayer mist M by application of an ultrasonic vibration to third liquid L3 in container 10.

Control unit 71 is implemented by a microcontroller, for example. Specifically, control unit 71 is implemented by a nonvolatile memory storing a program, a volatile memory used as a temporary storage area for execution of the program, an input/output port, a processor that executes the program, and the like. Control unit 71 may be implemented by a dedicated electronic circuit that realizes each operation.

Note that control unit 71 has only to be able to control voltage applying unit 40*a*, supplying unit 210, and mist-generating unit 401, and may control voltage applying unit 40*a*, supplying unit 210, and mist-generating unit 401 by transmitting a radio signal or may be connected to voltage applying unit 40*a*, supplying unit 210, and mist-generating unit 401 by a control line or the like.

According to the mist-generating method according to Variation 1 of Embodiment 1, unlike the mist-generating method according to Embodiment 1, atomized third liquid L3 containing functional droplet L is charged. That is, according to the mist-generating method according to Variation 1 of Embodiment 1, multilayer mist M having electric charge E is generated by charging a multilayer mist generated by mist-generating unit 401. In other words, in the mist-generating method according to Variation 1 of Embodiment 1, step S103 shown in FIG. 7 is performed after step S104 shown in FIG. 7.

Furthermore, mist-generating unit 401 of mist-generating device 100*a* according to Variation 1 of Embodiment 1 is an ultrasonic vibration generating device that generates multilayer mist M by atomizing third liquid L3 by applying an ultrasonic vibration to third liquid L3 containing functional droplet L. In addition, mist-generating device 100*a* includes charging electrode 30*a* for charging multilayer mist M.

With such a configuration, atomization and charging of third liquid L3 containing functional droplet L can be separately performed, so that the amount of multilayer mist M generated and the amount of charge of multilayer mist M can be separately controlled. Therefore, with such a configuration, the amount of multilayer mist M generated can be controlled to a desired amount.

(Variation 2)

Figure 9:
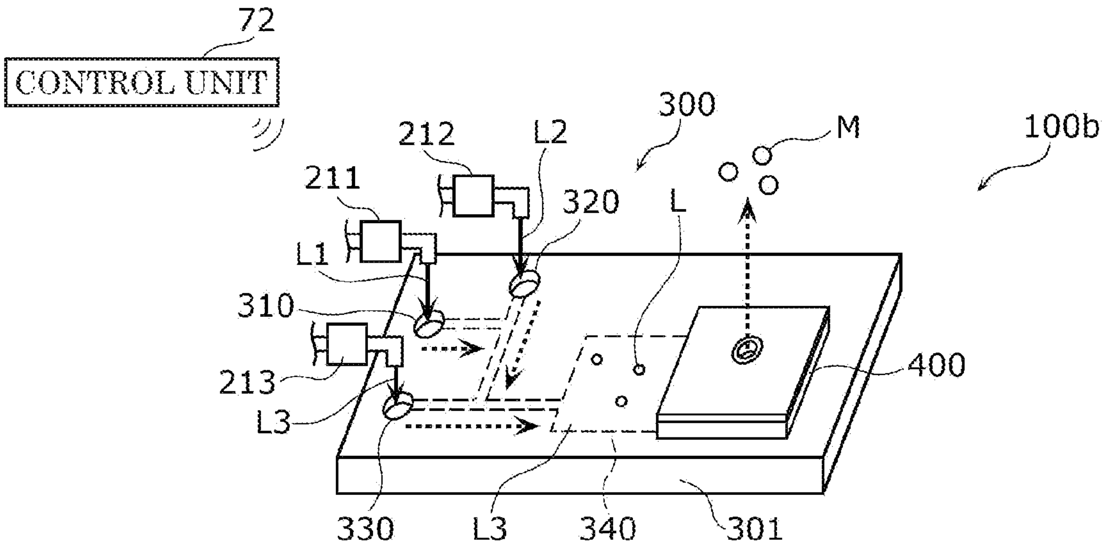
FIG. 9 is a schematic perspective view showing a configuration of a mist-generating device according to Variation 2 of Embodiment 1.
Figure 10:
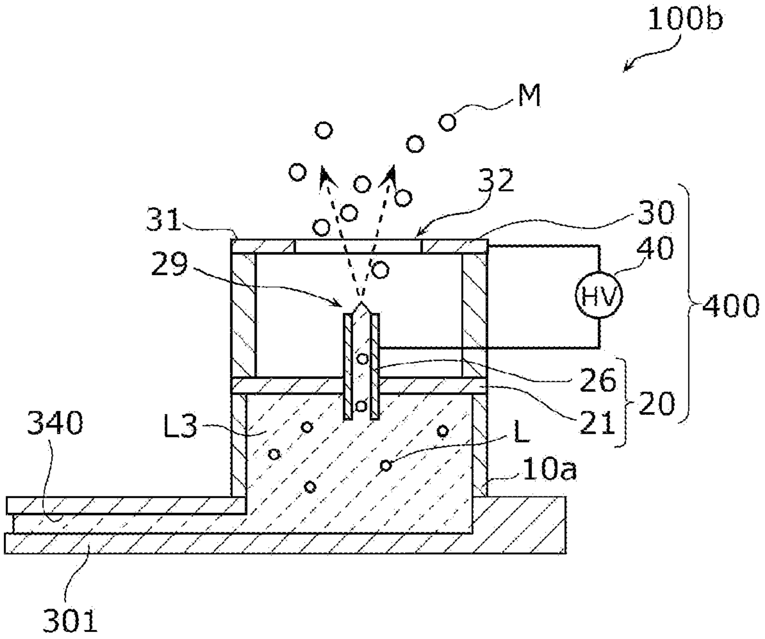
FIG. 10 is a partial enlarged cross-sectional view showing a configuration of the mist-generating device according to Variation 2 of Embodiment 1.

FIG. 9 is a perspective view showing a configuration of mist-generating device 100*b* according to Variation 2 of Embodiment 1. FIG. 10 is a partial enlarged cross-sectional view showing a configuration of mist-generating device 100*b* according to Variation 2 of Embodiment 1.

Note that the components of mist-generating device 100*b* according to Variation 2 of Embodiment 1 that are substantially the same as those of mist-generating device 100 according to Embodiment 1 are denoted by the same reference numerals, and descriptions thereof will be simplified or omitted. In FIG. 9, illustration of some components, such as voltage applying unit 40, is omitted.

Mist-generating device 100*b* includes droplet generating unit 300, mist-generating unit 400, and control unit 72. Droplet generating unit 300 includes microchannel chip 301, and supplying units 211, 212, and 213.

FIG. 9 is a schematic perspective view showing the whole of microchannel chip 301, which is mist-generating unit 400 shown in FIG. 4.

Microchannel chip 301 has first liquid inlet 310 to which first liquid L1 is introduced by supplying unit 211, second liquid inlet 320 to which second liquid L2 is introduced by supplying unit 212, and third liquid inlet 330 to which third liquid L3 is introduced by supplying unit 213. First liquid inlet 310 is connected to first liquid channel 311 shown in FIG. 4. Second liquid inlet 320 is connected to second liquid channel 321 shown in FIG. 4. Third liquid inlet 330 is connected to third liquid channel 331 shown in FIG. 4.

Supplying unit 211 supplies first liquid L1 to first liquid inlet 310 of microchannel chip 301. Supplying unit 211 is a pump, for example, and supplies first liquid L1 from a tank (not shown) containing first liquid L1 to first liquid inlet 310 through piping. Note that supplying unit 211 has only to be able to supply first liquid L1 to first liquid inlet 310 and may be provided with a solenoid valve or the like.

Supplying unit 212 supplies second liquid L2 to second liquid inlet 320 of microchannel chip 301. Supplying unit 212 is a pump, for example, and supplies second liquid L2 from a tank (not shown) containing second liquid L2 to second liquid inlet 320 through piping. Note that supplying unit 212 has only to be able to supply second liquid L2 to second liquid inlet 320 and may be provided with a solenoid valve or the like.

Supplying unit 213 supplies third liquid L3 to third liquid inlet 330 of microchannel chip 301. Supplying unit 213 is a pump, for example, and supplies third liquid L3 from a tank (not shown) containing third liquid L3 to third liquid inlet 330 through piping. Note that supplying unit 213 has only to be able to supply third liquid L3 to third liquid inlet 330 and may be provided with a solenoid valve or the like.

Microchannel chip 301 has reservoir 340.

Reservoir 340 is an accommodation unit that is connected to third liquid channel 331 and stores third liquid L3 containing functional droplet L.

As shown in FIG. 10, reservoir 340 is connected to container 10*a*.

Container 10*a* is a container that accommodates third liquid L3 containing functional droplet L. Container 10*a* is connected to reservoir 340 of microchannel chip 301 so that third liquid L3 containing functional droplet L can move therebetween. In this embodiment, container 10*a* is open at the bottom and connected to reservoir 340.

Control unit 72 shown in FIG. 9 is a controlling device that controls the overall operation of mist-generating device 100*b*. Specifically, control unit 72 controls operations of voltage applying unit 40 and supplying units 211, 212, and 213, for example. For example, control unit 72 controls voltage applying unit 40, thereby controlling the timing of application of a voltage between first electrode 30 and nozzle 26 and the magnitude of the voltage, for example.

Control unit 72 is implemented by a microcontroller, for example. Specifically, control unit 72 is implemented by a nonvolatile memory storing a program, a volatile memory used as a temporary storage area for execution of the program, an input/output port, a processor that executes the program, and the like. Control unit 72 may be implemented by a dedicated electronic circuit that realizes each operation.

Note that control unit 72 has only to be able to control voltage applying unit 40 and supplying units 211, 212, and 213, and may control voltage applying unit 40 and supplying units 211, 212, and 213 by transmitting a radio signal or may be connected to voltage applying unit 40 and supplying units 211, 212, and 213 by a control line or the like.

As described above, unlike mist-generating device 100 according to Embodiment 1, mist-generating device 100*b* does not include supplying unit 210, and third liquid L3 containing functional droplet L is supplied from droplet generating unit 300 to mist-generating unit 400. In other words, mist-generating device 100*b* includes droplet generating unit 300 that generates functional droplet L in third liquid L3, functional droplet L containing first liquid L1 that has a spherical shape and second liquid L2 that has a lower volatility than first liquid L1 and covers the whole of first liquid L1, and mist-generating unit 400 that generates multilayer mist M by atomizing third liquid L3 containing functional droplet L.

With such a configuration, third liquid L3 containing functional droplet L can be generated with an even simpler configuration, and multilayer mist M can be generated by atomizing generated third liquid L3 containing functional droplet L.

EMBODIMENT 2

In the following, a mist-generating device according to Embodiment 2 will be described.

[Configuration]

<Overview>

First, with reference to FIGS. 11 to 15, an overview of multilayer mist BM and a configuration of a mist-generating device that generates multilayer mist BM will be described.

Figure 11:
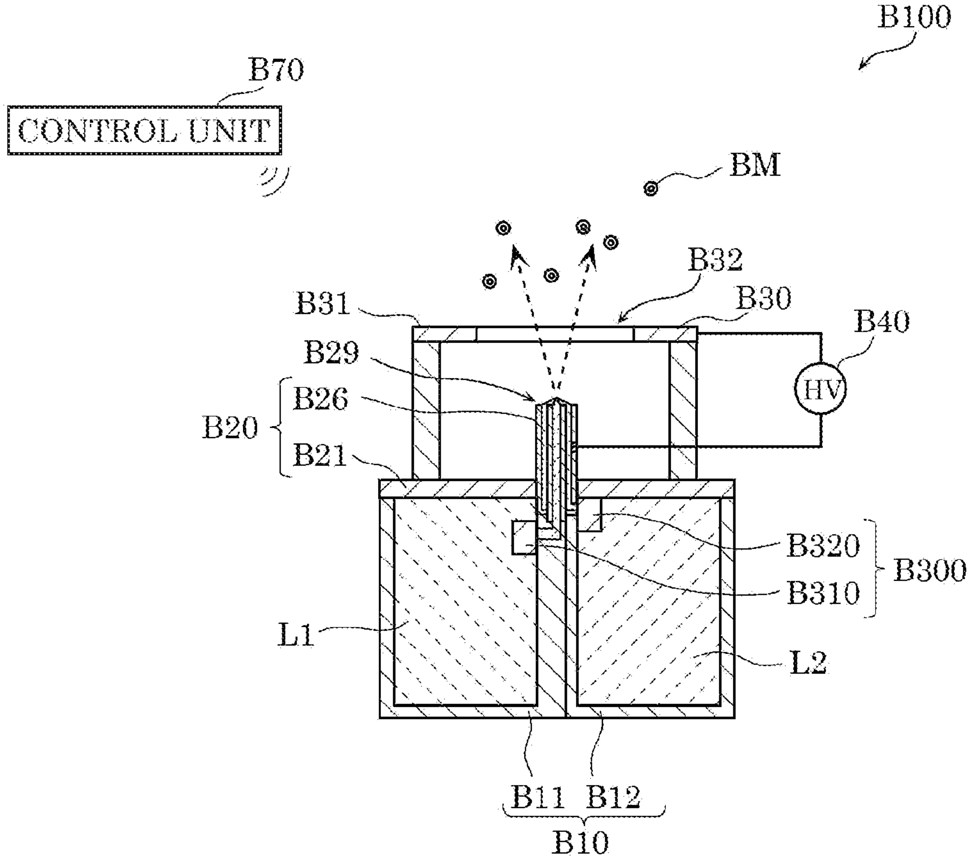
FIG. 11 is a schematic cross-sectional view showing a configuration of a mist-generating device according to Embodiment 2.

FIG. 11 is a schematic cross-sectional view showing a configuration of mist-generating device B100 according to Embodiment 2.

As shown in FIG. 11, mist-generating device B100 according to Embodiment 2 includes container B10, ejection plate B20, first electrode B30, voltage applying unit B40, supplying unit B300, and control unit B70. Ejection plate B20 includes electrode support plate B21 and nozzle B26.

FIG. 11 shows control unit B70 as a functional block. Control unit B70 is implemented by a microcomputer (microcontroller), for example, and is arranged inside an outer housing (not shown) of mist-generating device B100. Control unit B70 may be attached to the exterior of container B10, for example.

Mist-generating device B100 is a spray device that ejects multilayer mist BM capable of floating in the air formed by atomizing first liquid L1 and second liquid L2. For example, mist-generating device B100 is a device that generates multilayer mist BM having a disinfection effect or sanitization effect by applying a high voltage to first liquid L1 and second liquid L2 to produce an electrostatic force and atomizing first liquid L1 and second liquid L2 by the action of the produced electrostatic force. "Multilayer mist BM" refers to a mist formed by atomizing first liquid L1 and second liquid L2 or one of a plurality of liquid particles forming the mist. Mist-generating device B100 is used for a disinfecting device or a sanitizing device, for example.

Note that when first liquid L1 contains an aromatic constituent, for example, mist-generating device B100 is an aroma generator that generates multilayer mist BM containing an aromatic constituent.

In mist-generating device B100, supplying unit B300 feeds first liquid L1 and second liquid L2 in container B10 to nozzle B26 to introduce first liquid L1 and second liquid L2 to a tip end of nozzle B26, and a large number of multilayer mists BM formed by atomizing first liquid L1 and second liquid L2 are ejected from opening B29 provided at the tip end of nozzle B26.

Specifically, voltage applying unit B40 applies a high voltage between first electrode B30 and nozzle B26, which is an example of a second electrode, thereby causing ejection of a mist of first liquid L1 and second liquid L2 (that is, a large number of multilayer mists BM) from opening B29 of nozzle B26. Here, the "high voltage" is on the order of 5 kV with respect to a ground voltage (0 V), for example, but is not particularly limited. Note that the voltage of first electrode B30 may be positive or negative with respect to the ground voltage.

A channel that introduces first liquid L1 and second liquid L2 to opening B29 in container 10 is formed in nozzle B26. First liquid L1 and second liquid L2 having flowed in the channel and exited opening B29 are changed in shape by the electric field to form a Taylor cone. First liquid L1 and second liquid L2 are atomized at the tip end of the Taylor cone to form multilayer mist BM.

Note that, although FIG. 11 shows one nozzle B26, the number of nozzles B26 provided on ejection plate B20 is not particularly limited and may be two, or three or more.

Multilayer mist BM generated at the tip end of nozzle B26 is discharged toward first electrode B30. In order to discharge multilayer mist BM in the forward direction beyond first electrode B30, through-hole B32 is formed in flat plate part B31 of first electrode B30 at a position directly opposed to nozzle B26. This allows multilayer mist BM to be discharged through through-hole B32 in the forward direction beyond first electrode B30. Here, the "forward direction" refers to a direction in which multilayer mist BM is discharged and is the opposite direction to nozzle B26 with respect to first electrode B30.

Figure 12:
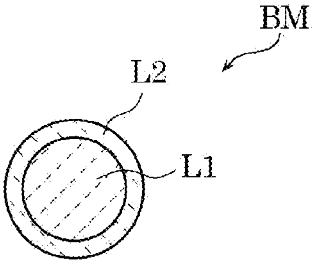
FIG. 12 is a cross-sectional view showing a configuration of floatable functional particle according to Embodiment 2.

FIG. 12 is a cross-sectional view showing a configuration of multilayer mist BM according to Embodiment 2.

Multilayer mist BM is a fine liquid particle having a diameter of the order of nanometers or micrometers, and is capable of floating in the air. For example, the outer diameter of multilayer mist BM is on the order of several tens of μm. Note that the outer diameter of multilayer mist BM is preferably equal to or smaller than 10 μm. More preferably, the diameter of a liquid particle forming multilayer mist BM is equal o or greater than 10 nm and equal to or smaller than 3 μm.

Multilayer mist BM contains first liquid L1 that has a spherical shape and second liquid L2 that has a film-like shape and covers the whole of first liquid L1.

First liquid L1 is a liquid particle that has a predetermined function (effect). For example, first liquid L1 is a liquid particle containing an aromatic constituent that has a function of generating an aroma when coming into contact with air, or a liquid particle that has a function of killing a target such as a fungus when coming into contact with the target.

Second liquid L2 is a liquid having a film-like shape that has a lower volatility than first liquid L1 and covers the whole of first liquid L1. In other words, second liquid L2 is a liquid that covers the whole of first liquid L1 and is less susceptible to volatilization than first liquid L1. That is, the volatility of second liquid L2 is lower than the volatility of first liquid L1. Second liquid L2 is formed in a film-like shape to cover the whole of first liquid L1.

Second liquid L2 is formed to have a thickness that allows second liquid L2 to volatilize or be lost before multilayer mist BM reaches to a predetermined distance from the location where the mist is generated (that is, mist-generating device B100) so that first liquid L1 is exposed and comes into contact with air. Specifically, second liquid L2 is formed to have a thickness that allows second liquid L2 to volatilize or be lost to allow first liquid L1 to be exposed and come into contact with air when a predetermined time has elapsed or, in other words, when multilayer mist BM generated by mist-generating device B100 has moved a predetermined distance. The predetermined distance can be arbitrarily determined. The thickness of second liquid L2 of multilayer mist BM can be any thickness as far as second liquid L2 completely volatilizes when a predetermined time, which is arbitrarily determined in advance, has elapsed or, in other words, when multilayer mist BM has moved the predetermined distance. For example, the thickness of second liquid L2 of multilayer mist BM can be approximately equal to the radius of first liquid L1 of multilayer mist BM, greater than the radius of first liquid L1, or smaller than the radius of first liquid L1.

In order to prevent mixing of first liquid L1 and second liquid L2 in multilayer mist BM, for example, one of first liquid L1 and second liquid L2 is oily, and the other is aqueous. That is, one of first liquid L1 and second liquid L2 is oily, and the other is aqueous.

In the following, each component of mist-generating device B100 will be described in detail.

<Container>

Container B10 is a container that accommodates first liquid L1 and second liquid L2. Container B10 includes first accommodation unit B11 that accommodates first liquid L1 and second accommodation unit B12 that accommodates second liquid L2.

First accommodation unit B11 is a space that accommodates first liquid L1. First liquid L1 is a liquid that delivers a predetermined function when coming into contact with air, for example. When mist-generating device B100 is an aroma generator, for example, first liquid L1 is an oily liquid containing an aromatic constituent. When mist-generating device B100 is a disinfecting device, for example, first liquid L1 is an aqueous liquid containing a disinfection constituent such as hypochlorous acid. Note that, when first liquid L1 and second liquid L2 are atomized in an electrostatic atomization process as in this embodiment, first liquid L1 may be water.

Second accommodation unit B12 is a space that accommodates second liquid L2. When first liquid L1 is an oily liquid containing an aromatic constituent, for example, second liquid L2 is an aqueous liquid having a lower volatility than first liquid L1. When first liquid L1 is an aqueous liquid containing a disinfection constituent such as hypochlorous acid, for example, second liquid L2 is an oily liquid. Second liquid L2 is formed in a film-like shape.

For example, second liquid L2 has a lower volatility than first liquid L1. That is, second liquid L2 may be a material that is less susceptible to volatilization than first liquid L1.

Container B10 is made of a metal material such as stainless steel, for example. However, container B10 may be made of a resin material. Container B10 may be made of a material having one or both of acid resistance and alkali resistance.

Container B10 has the shape of a cylinder with an open top, for example. However, the shape of container B10 is not limited thereto. Container B10 may have the shape of a cube, a rectangular parallelepiped, or a flat tray. The open top of container B10 is covered by ejection plate B20.

<Ejection Plate>

Figure 13:
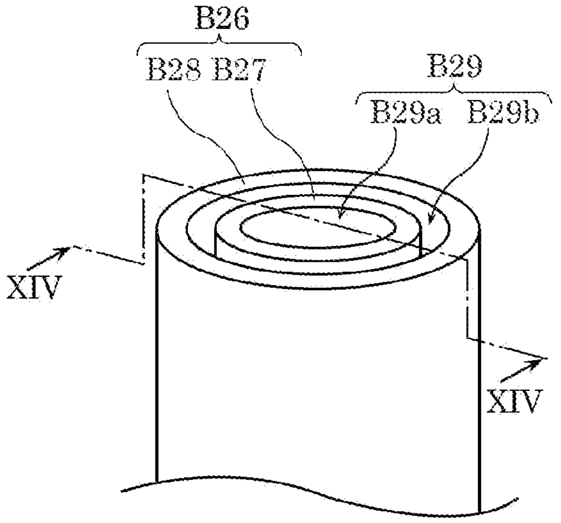
FIG. 13 is a schematic perspective view of a nozzle according to Embodiment 2.
Figure 14:
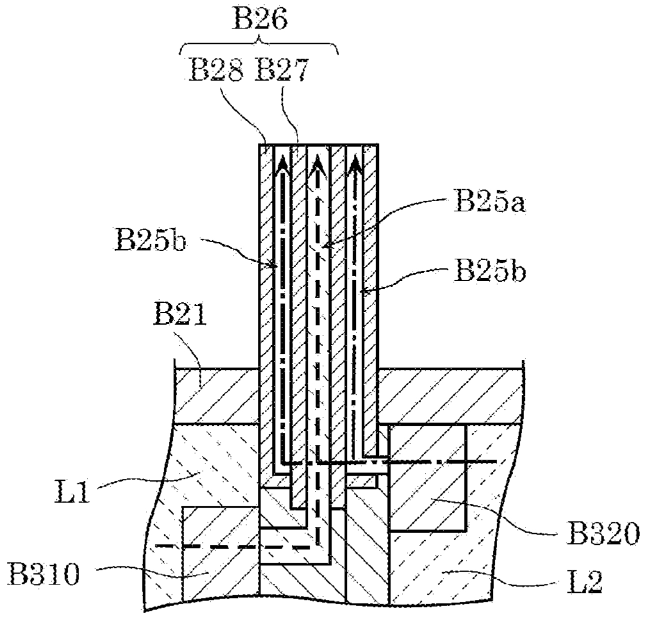
FIG. 14 is a partial enlarged cross-sectional view showing a cross section of the nozzle taken along the line XIV-XIV in FIG. 13.

FIG. 13 is a schematic perspective view of nozzle B26 according to Embodiment 2. FIG. 14 is a partial enlarged cross-sectional view showing a cross section of nozzle B26 taken along the line XIV-XIV in FIG. 13.

Ejection plate B20 has opening B29 through which first liquid L1 and second liquid L2 are ejected. Specifically, ejection plate B20 includes electrode support plate B21 having a planar shape, and nozzle B26. First discharging port B29*a* and second discharging port B29*b* of opening B29 are provided at a tip end of nozzle B26. More specifically, as shown in FIG. 13, nozzle B26 has inner first discharging port B29*a* and outer second discharging port B29*b* that are concentrically formed. In FIG. 13, nozzle B26 has inner first discharging port B29*a* and outer second discharging port B29*b* that are concentrically formed.

As shown in FIG. 14, first liquid L1 is discharged from first discharging port B29*a* of nozzle B26 through first channel B25*a*. Second liquid L2 is discharged from second discharging port B29*b* of nozzle B26 through second channel B25*b* in such a manner as to cover first liquid L1 discharged from first discharging port B29*a*. In this way, mist-generating device B100 generates multilayer mist BM containing first liquid L1 having a spherical shape and second liquid L2 having a film-like shape covering the whole of first liquid L1.

Electrode support plate B21 is a plate-like member that supports nozzle B26. Electrode support plate B21 is made of a resin material, for example. However, electrode support plate B21 may be made of a metal material. Electrode support plate B21 may be made of a material having one or both of acid resistance and alkali resistance.

Nozzle B26 is fixed to electrode support plate B21 by press-fitting. For example, a through-hole is formed in electrode support plate B21 at a location where opening B29 is to be provided, and nozzle B26 is inserted into the through-hole and fixed. Electrode support plate B21 is a flat plate having a uniform thickness. However, the present invention is not thereto, and electrode support plate B21 may be a curved plate.

Electrode support plate B21 is fixed to container B10. Note that electrode support plate B21 may be made of the same material as container B10 and formed integrally with container B10.

Nozzle B26 is connected to container B10 and discharges first liquid L1 and second liquid L2 in container B10 to the outside of container B10. Specifically, nozzle B26 is connected to first accommodation unit B11 and second accommodation unit B12 by first channel B25*a* and second channel B25*b*. Nozzle B26 discharges first liquid L1 in first accommodation unit B11 from first discharging port B29*a* through first channel B25*a*, and discharges second liquid L2 in second accommodation unit B12 from second discharging port B29*b* through second channel B25*b*. Nozzle B26 projects toward first electrode B30 from electrode support plate B21. Nozzle B26 has an opening at a rear end thereof (that is, an end on the side of container B10), and a channel extending from the opening to opening B29.

Note that at least one of the inner and outer diameters of nozzle B26 may be tapered from the rear end toward the tip end. For example, opening B29 at the tip end may be smaller than the opening at the rear end, and the channel connecting these openings may have the shape of a truncated cone. Here, note that the inner diameter (bore diameter) of first discharging port B29*a* and the inner diameter (bore diameter) of second discharging port B29*b* are the inner diameters (bore diameters) of first nozzle part B27 and second nozzle part B28 at the rear end closer to first electrode B30.

The rear end of nozzle B26 is positioned at a location where the rear end is in contact with first liquid L1 and second liquid L2 in container B10. Specifically, the rear end of nozzle B26 is located in such a manner that the channels formed in nozzle B26 are in communication with the interiors of first accommodation unit B11 and second accommodation unit B12.

As shown in FIGS. 13 and 14, first supplying unit B310 introduces first liquid L1 from the opening at the rear end of nozzle B26 to first discharging port B29*a* at the tip end through first channel B25*a* in nozzle B26. Second supplying unit B320 introduces second liquid L2 from the opening at the rear end of nozzle B26 to second discharging port B29*b* at the tip end through second channel B25*b*.

Nozzle B26 stands perpendicularly to a principal surface (specifically, an upper surface) of electrode support plate B21. The principal surface is a surface of electrode support plate B21 that is opposed to first electrode B30 and is on the opposite side to first liquid L1 and second liquid L2. The ratio of height to outer diameter (referred to as an aspect ratio, hereinafter) of nozzle B26 is preferably equal to or greater than 4. Here, the height of nozzle B26 is represented by the distance from the tip end of nozzle B26 to the principal surface of electrode support plate B21. The height is equal to or greater than 2 mm, for example. The greater the aspect ratio of nozzle B26, the more easily the electric field is concentrated at the tip end of nozzle B26. Therefore, the aspect ratio of nozzle B26 can be equal to or greater than 6, for example.

The material of nozzle B26 is not particularly limited. For example, nozzle B26 may be a metal material having a conductivity, such as stainless steel. For example, if first nozzle part B27 is made of a conductive material, first nozzle part B27 can serve as a second electrode paired with first electrode B30. That is, at least a part of first nozzle part B27 may be formed as a second electrode paired with first electrode B30. The second electrode (nozzle B26 in this embodiment) is paired with first electrode B30, and a voltage is applied to at least one of first liquid L1 and second liquid L2 discharged from nozzle B26 to produce multilayer mist BM.

Second nozzle part B28 may be made of a metal material having a conductivity, such as stainless steel, or may be made of a material having insulation properties, such as resin.

Note that mist-generating device B100 may be provided with an electrode housed in each of first accommodation unit B11 and second accommodation unit B12 and paired with first electrode B30, as a second electrode, for example. In that case, first nozzle part B27 may be made of a material having insulation properties, such as resin. First nozzle part B27 may be made of a material having one or both of acid resistance and alkali resistance.

Voltage applying unit B40 may be electrically connected to second nozzle part B28. With such a configuration, a voltage can be more easily applied to second liquid L2. In that case, second nozzle part B28 can be made of a conductive material.

<First Electrode>

First electrode B30 is an opposed electrode that is arranged outside container B10 in such a manner that through-hole B32 is opposed to opening B29. Specifically, first electrode B30 is arranged outside container B10 to be opposed to nozzle B26 serving also as a second electrode paired with first electrode B30. When a voltage is applied between first electrode B30 and nozzle B26, first liquid L1 and second liquid L2 are discharged from the tip end of nozzle B26 and atomized. First electrode B30 is arranged in parallel with electrode support plate B21 of ejection plate B20, for example. Specifically, a rear surface of first electrode B30 is in parallel with the principal surface of electrode support plate B21.

First electrode B30 is made of a metal material having a conductivity, such as stainless steel. First electrode B30 may be made of a material having one or both of acid resistance and alkali resistance.

First electrode B30 includes flat plate part B31 and through-hole B32. Flat plate part B31 is conductive and is electrically connected to voltage applying unit B40. Flat plate part B31 has a substantially uniform thickness. Nozzle B26 (more specifically, first nozzle part B27) is also conductive and is electrically connected to voltage applying unit B40.

Through-hole B32 passes through flat plate part B31 in the thickness direction (that is, the back-and-forth direction). Through-hole B32 is provided to allow atomized first liquid L1 and second liquid L2 ejected from opening B29, that is, multilayer mist BM, to pass through flat plate part B31. Through-hole B32 has a flat cylindrical shape. The shape of the opening of through-hole B32 is not limited to a circle but can be a square, a rectangle, or an ellipse, for example.

The diameter of the opening of through-hole B32 is not particularly limited. For example, the diameter falls within a range from 1 mm to 2.25 mm inclusive. The diameter of the opening of through-hole B32 may be five or more times greater than and ten or less times smaller than the outer diameter of nozzle B26. Multilayer mist BM discharged from the tip end of the Taylor cone spreads in a conical shape. Therefore, the greater the diameter of the opening of through-hole B32, the more multilayer mist BM passes through through-hole B32.

<Voltage Applying Unit>

Voltage applying unit B40 applies a predetermined voltage between first liquid L1 and second liquid L2 and first electrode B30. Specifically, voltage applying unit B40 is electrically connected to first electrode B30 and nozzle B26 (more specifically, first nozzle part B27) by metal wiring or the like, and applies a voltage so as to produce a predetermined potential difference between first electrode B30 and first nozzle part B27. For example, first nozzle part B27 is grounded, and voltage applying unit B40 applies the ground potential to first liquid L1 and second liquid L2. Voltage applying unit B40 applies a potential to first electrode B30, thereby applying a predetermined voltage between first electrode B30 and first liquid L1 and second liquid L2. Note that first electrode B30 may be at the ground potential.

The predetermined voltage applied by voltage applying unit B40 is a direct-current voltage equal to or higher than 3.5 kV and equal to or lower than 10 kV. Alternatively, the predetermined voltage may be equal to or higher than 4.5 kV and equal to or lower than 8.5 kV. Note that the predetermined voltage may be a pulse voltage, a pulsating voltage, or an alternating-current voltage.

Specifically, voltage applying unit B40 is implemented by a power supply circuit including a converter or the like. For example, voltage applying unit B40 applies a voltage to first liquid L1 and second liquid L2 by generating a predetermined voltage based on an electric power received from an external power supply, such as a utility power supply, and applying the generated voltage between first electrode B30 and the second electrode.

<Supplying Unit>

Supplying unit B300 feeds first liquid L1 and second liquid L2 in container B10 to nozzle B26. Supplying unit B300 includes first supplying unit B310 and second supplying unit B320, for example.

First supplying unit B310 supplies first liquid L1 to first discharging port B29*a* through first channel B25*a* formed in nozzle B26. Specifically, first supplying unit B310 is a pump that feeds first liquid L1 in first accommodation unit B11 to first discharging port B29*a* through first channel B25*a* formed in nozzle B26 (specifically, first nozzle part B27).

Second supplying unit B320 supplies second liquid L2 to second discharging port B29*b* through second channel B25*b* formed in nozzle B26. Specifically, second supplying unit B320 is a pump that feeds second liquid L2 in second accommodation unit B12 to second discharging port B29*b* through second channel B25*b* formed in nozzle B26, or more specifically, defined by an outer side surface of first nozzle part B27 and an inner side surface of second nozzle part B28.

<Control Unit>

Control unit B70 is a controlling device that controls the overall operation of mist-generating device B100. Specifically, control unit B70 controls operations of voltage applying unit B40 and supplying unit B300. For example, control unit B70 controls voltage applying unit B40, thereby controlling the timing of application of a voltage between first electrode B30 and nozzle B26 and the magnitude of the voltage, for example.

Figure 15:
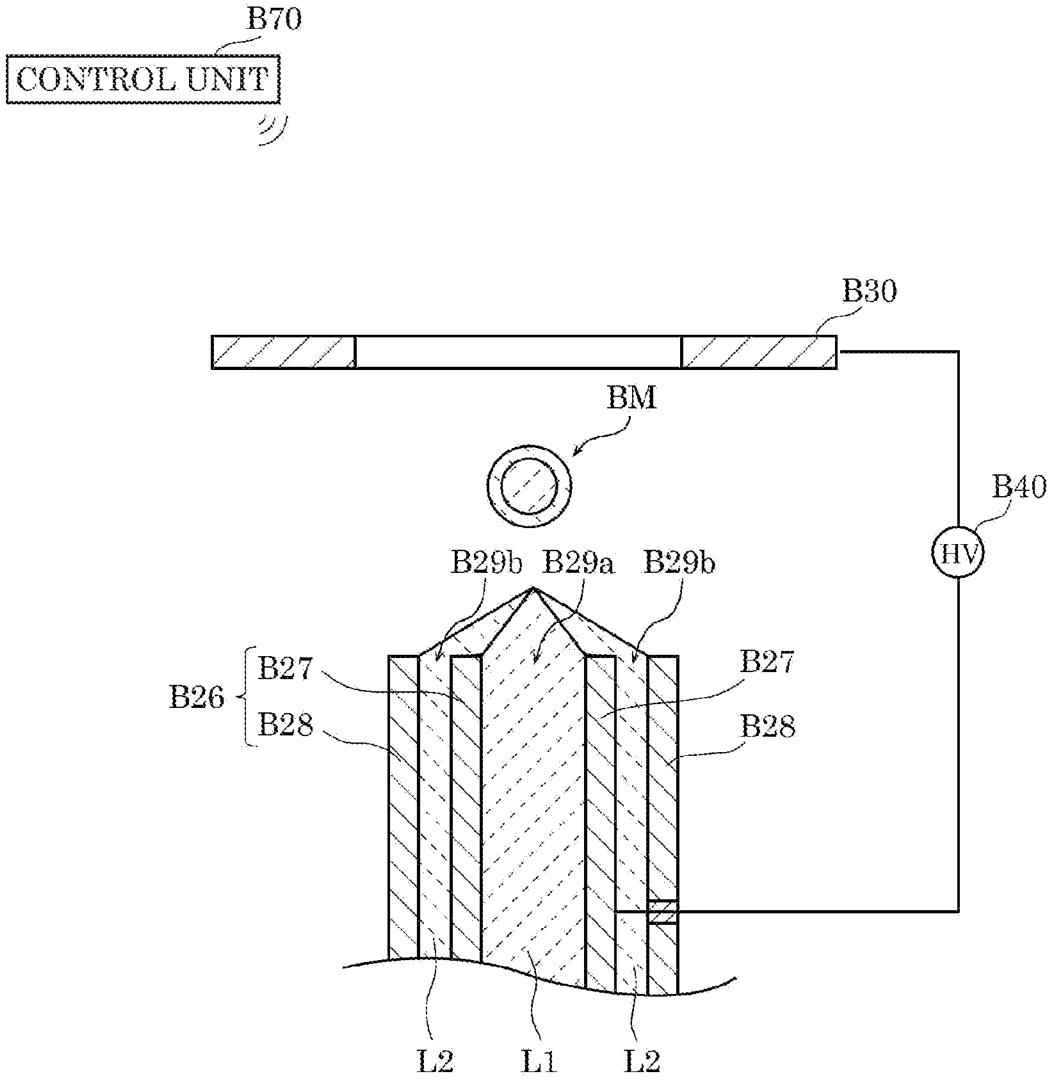
FIG. 15 is a schematic cross-sectional view schematically showing how the mist-generating device according to Embodiment 2 generates a floatable functional particle.

FIG. 15 is a schematic cross-sectional view schematically showing how multilayer mist BM is generated by mist-generating device B100 according to Embodiment 2.

As shown in FIGS. 14 and 15, control unit B70 controls supplying unit B300 and voltage applying unit B40 to discharge first liquid L1 from first discharging port B29*a* and discharge second liquid L2 having a lower volatility than first liquid L1 from second discharging port B29*b*, thereby generating multilayer mist BM containing first liquid L1 having a spherical shape and second liquid L2 having a film-like shape covering the whole of first liquid L1.

If control unit B70 appropriately controls first supplying unit B310 and voltage applying unit B40, first liquid L1 discharged from nozzle B26 forms a neat Taylor cone. This means that the amount of first liquid L1 fed to nozzle B26 is appropriate. Similarly, if control unit B70 appropriately controls second supplying unit B320 and voltage applying unit B40, second liquid L2 discharged from nozzle B26 forms a neat Taylor cone. Control unit B70 controls supplying unit B300 to appropriately control the amounts of first liquid L1 and second liquid L2 fed by supplying unit B300.

Control unit B70 also controls the thickness of second liquid L2 in multilayer mist BM by controlling the amount of first liquid L1 supplied by supplying unit B300 (specifically, first supplying unit B310), for example. Specifically, control unit B70 controls the thickness of second liquid L2 in multilayer mist BM by controlling at least one of the amount of first liquid L1 supplied by first supplying unit B310 and the amount of second liquid L2 supplied by second supplying unit B320.

Control unit B70 is implemented by a microcontroller, for example. Specifically, control unit B70 is implemented by a nonvolatile memory storing a program, a volatile memory used as a temporary storage area for execution of the program, an input/output port, a processor that executes the program, and the like. Control unit B70 may be implemented by a dedicated electronic circuit that realizes each operation.

Note that control unit B70 has only to be able to control voltage applying unit B40 and supplying unit B300, and may control voltage applying unit B40 and supplying unit B300 by transmitting a radio signal or may be connected to voltage applying unit B40 and supplying unit B300 by a control line or the like.

[Effects and the like]

As described above, multilayer mist BM according to Embodiment 2 is a floatable functional particle capable of floating in the air. Multilayer mist BM contains first liquid L1 having a spherical shape that has a predetermined function, and second liquid L2 having a film-like shape that has a lower volatility than first liquid L1 and covers the whole of first liquid L1.

Figure 16:
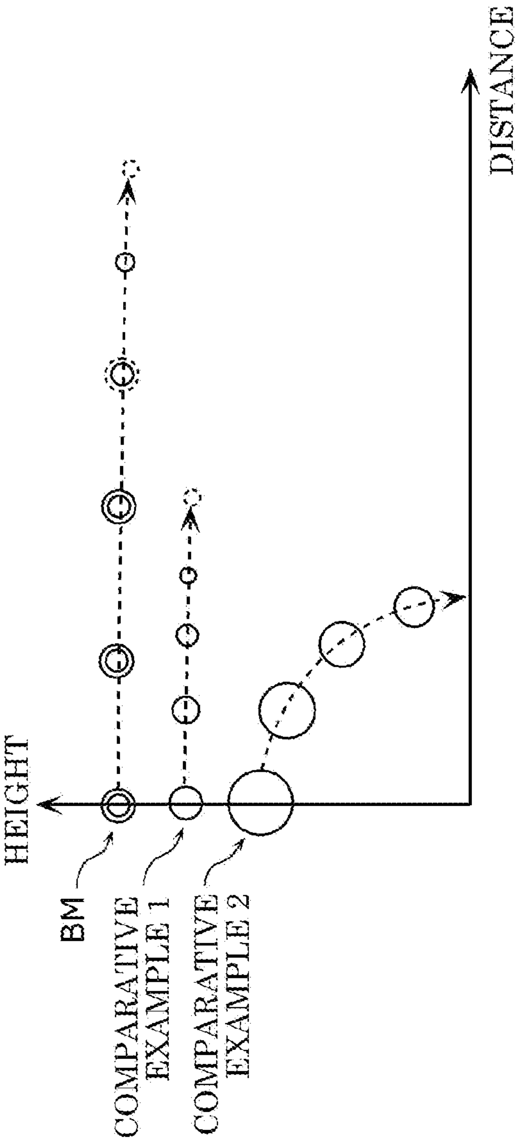
FIG. 16 is a schematic diagram for illustrating an effect of the floatable functional particle according to Embodiment 2.

FIG. 16 is a schematic diagram for illustrating an effect of multilayer mist BM according to Embodiment 2.

As shown in FIG. 16, with a conventional nanomist according to comparative example 1, a functional droplet that delivers a function when coming into contact with air is exposed and therefore immediately vaporizes after the functional droplet is discharged into the air.

A conventional mist according to comparative example 2 has a large particle diameter of the order of several hundreds of μm in order to prevent immediate vaporization of the mist. However, the mist falls soon under its own weight and cannot travel far.

Multilayer mist BM has a structure in which first liquid L1 that delivers a function when coming into contact with air is covered by second liquid L2.

With multilayer mist BM thus configured, second liquid L2 first vaporizes, and first liquid L1 then vaporizes. Therefore, if the thickness of second liquid L2 is appropriately adjusted, multilayer mist BM is likely to be able to float in the air for a desired floating time. In this way, the floating time of multilayer mist BM in the air can be extended compared with conventional mists.

For example, one of first liquid L1 and second liquid L2 is oily, and the other is aqueous.

With such a configuration, first liquid L1 and second liquid L2 are unlikely to be mixed. Therefore, with such a configuration, the floating time of multilayer mist BM in the air can be further extended.

For example, the particle diameter of multilayer mist BM is equal to or smaller than 10 μm. According to the prediction by the present inventors, when the particle diameter of multilayer mist BM is 5 μm, for example, the floating time of multilayer mist BM in the air is about 20 minutes. Furthermore, according to the prediction by the present inventors, when the particle diameter of multilayer mist BM is 3 μm, for example, the floating time of multilayer mist BM in the air is about 60 minutes. Furthermore, according to the prediction by the present inventors, when the particle diameter of multilayer mist BM is 1 μm, for example, the floating time of multilayer mist BM in the air is about 550 minutes. Here, the thickness of the film of second liquid L2 is reduced as the particle diameter of multilayer mist BM decreases. For example, the thickness of the film of second liquid L2 is equal to or smaller than 80 nm when the particle diameter of multilayer mist BM is 5 μm, is equal to or smaller than 50 nm when the particle diameter of multilayer mist BM is 3 μm, and is equal to or smaller than 15 nm when the particle diameter of multilayer mist BM is 1 μm. If the floating time of multilayer mist BM in the air can be extended in this way, a larger number of multilayer mists BM are likely to come into contact with the surface of a person in the living space of the person. Therefore, if multilayer mist BM has the sizes described above, the chances can be increased that multilayer mist BM comes into contact with the surface of a human body, and second liquid L2 disappears, that is, multilayer mist BM comes into contact with the surface of a human body, and first liquid L1 having been covered by second liquid L2 is exposed, and as a result, first liquid L1 becomes able to exert its effect, such as disinfection effect, on the human body (the face, in particular).

If multilayer mist BM has the sizes described above, multilayer mist BM does not fall soon under its own weight and can float in the air for an extended time.

Furthermore, mist-generating device B100 according to Embodiment 2 includes nozzle B26 having inner first discharging port B29*a* and outer second discharging port B29*b* that are concentrically formed, and control unit B70 that controls first discharging port B29*a* to discharge first liquid L1 and second discharging port B29*b* to discharge second liquid L2 having a lower volatility than first liquid L1 so as to generate multilayer mist BM floating in the air that contains first liquid L1 having a spherical shape and second liquid L2 covering the whole of first liquid L1.

With such a configuration, mist-generating device B100 can generate multilayer mist BM having a longer floating time in the air than conventional described above.

Furthermore, mist-generating device B100 includes first supplying unit B310 that supplies first liquid L1 to first discharging port B29*a* through first channel B25*a* formed in nozzle B26, and second supplying unit B320 that supplies second liquid L2 to second discharging port B29*b* through second channel B25*b*, which is different from first channel B25*a*, that is formed in nozzle B26. Control unit B70 further controls the thickness of second liquid L2 (that is, second liquid L2) in multilayer mist BM by controlling at least one of the amount of first liquid L1 supplied by first supplying unit B310 and the amount of second liquid L2 supplied by second supplying unit B320.

With such a configuration, mist-generating device B100 can generate multilayer mist BM containing second liquid L2 having a variable thickness under the control of control unit B70. Therefore, with such a configuration, mist-generating device B100 can generate multilayer mist BM having a dwell time in the air that is appropriate to the size of the space in which mist-generating device B100 is installed.

Mist-generating device B100 further includes first electrode B30 arranged to be opposed to nozzle B26, and a second electrode paired with first electrode B30 that applies a voltage to at least one of first liquid L1 and second liquid L2 discharged from nozzle B26 to generate multilayer mist BM, for example.

With such a configuration, mist-generating device B100 can simply generate multilayer mist BM having a particle diameter of the order of nanometers to micrometers.

In mist-generating device B100, at least part of first nozzle part B27 is formed as a second electrode.

With such a configuration, mist-generating device B100 can generate multilayer mist BM with a simpler configuration without a separate member serving as a second electrode.

(Variation 1)

Figure 17:
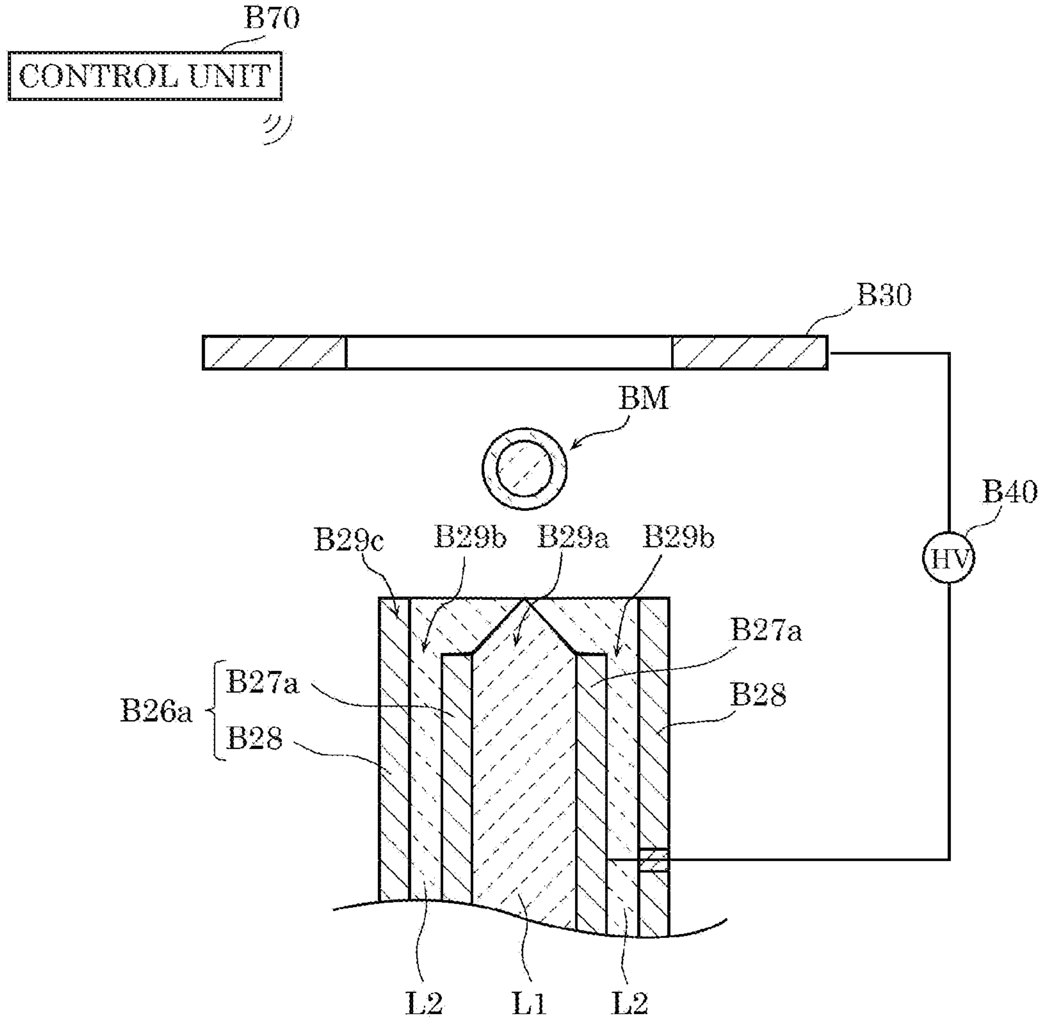
FIG. 17 is a schematic cross-sectional view showing a configuration of a nozzle of a mist-generating device according to Variation 1 of Embodiment 2.

FIG. 17 is a schematic cross-sectional view showing a configuration of nozzle B26*a* of a mist-generating device according to Variation 1 of Embodiment 2.

Note that the mist-generating device according to Variation 1 of Embodiment 2 has the same components as those of mist-generating device B100 according to Embodiment 2 except for the nozzle thereof. Referring to FIG. 8, the components of the mist-generating device according to Variation 1 of Embodiment 2 that are substantially the same as those of mist-generating device B100 according to Embodiment 2 are denoted by the same reference numerals, and descriptions thereof will be simplified or omitted.

As shown in FIG. 17, nozzle B26*a* includes first nozzle part B27*a* and second nozzle part B28. Specifically, nozzle B26*a* includes first nozzle part B27*a* that has first discharging port B29*a*, and second nozzle part B28 that covers an outer side surface of first nozzle part B27*a* at a distance in the radial direction to define second discharging port B29*b* with first nozzle part B27*a*. Here, nozzle B26*a* differs from nozzle B26 in that the end part of first nozzle part B27*a* in which first discharging port B29*a* is formed is retracted from end part B29*c* of second nozzle part B28.

For example, second liquid L2 may be difficult to form a Taylor cone like that of first liquid L1, depending on the material. In such a case, if the end part of first nozzle part B27*a* in which first discharging port B29*a* is formed is retracted from end part B29*c* of second nozzle part B28 as shown in FIG. 17, multilayer mist BM containing a film of second liquid L2 having a desired thickness (see FIG. 12) can be generated as with mist-generating device 100 according to Embodiment 2 shown in FIG. 15.

As described above, for example, nozzle B26*a* of the mist-generating device according to Variation 1 of Embodiment 2 includes first nozzle part B27*a* that has first discharging port B29*a*, and second nozzle part B28 that covers an outer side surface of first nozzle part B27*a* at a distance in the radial direction to define second discharging port B29*b* with first nozzle part B27*a*. The end part of first nozzle part B27*a* in which first discharging port B29*a* is formed is retracted from end part B29*c* of second nozzle part B28.

With such a configuration, even when second liquid L2 is difficult to form a Taylor cone like that of first liquid L1, for example, multilayer mist BM containing a film of second liquid L2 having a desired thickness can be generated.

(Variation 2)

Figure 18:
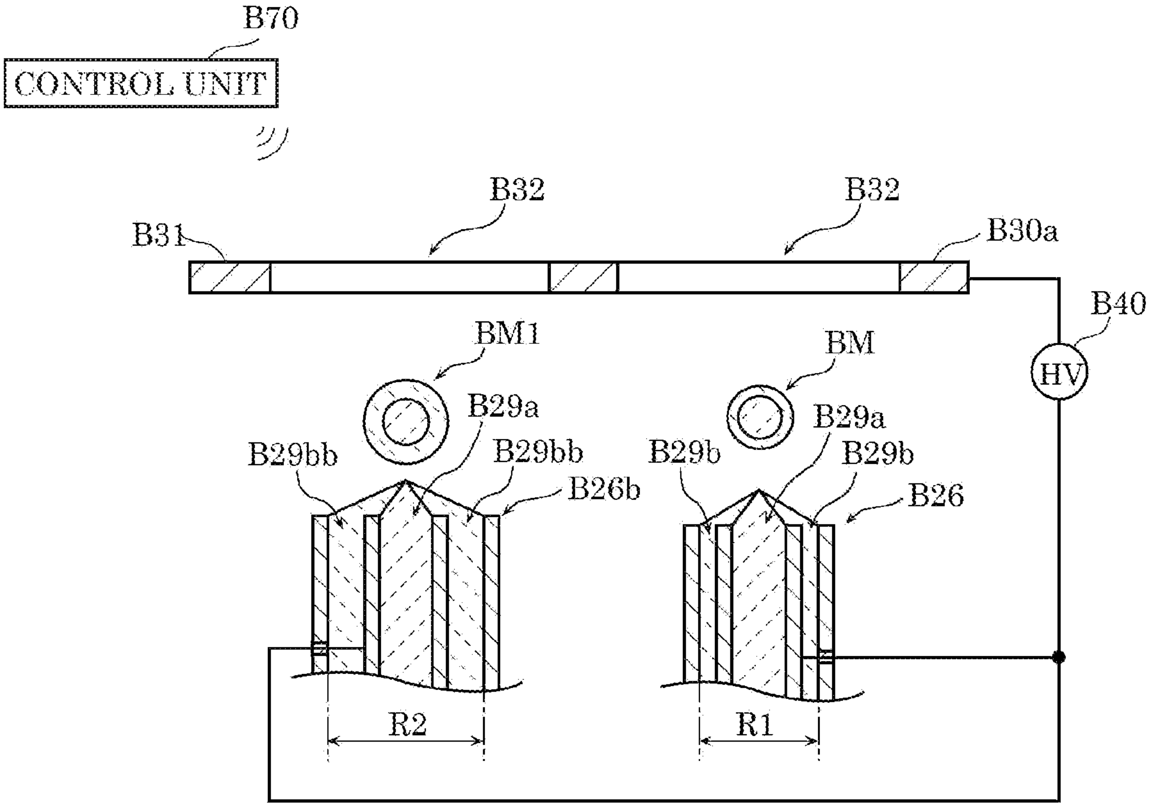
FIG. 18 is a schematic cross-sectional view showing a configuration of a nozzle of a mist-generating device according to Variation 2 of Embodiment 2.

FIG. 18 is a schematic cross-sectional view showing a configuration of a nozzle of a mist-generating device according to Variation 2 of Embodiment 2.

Note that the mist-generating device according to Variation 2 of Embodiment 2 has the same components as those of mist-generating device B100 according to Embodiment 2 except for the nozzle thereof. Referring to FIG. 18, the components of the mist-generating device according to Variation 2 of Embodiment 2 that are substantially the same as those of mist-generating device B100 according to Embodiment 2 are denoted by the same reference numerals, and descriptions thereof will be simplified or omitted.

As shown in FIG. 18, the mist-generating device according to Variation 2 of Embodiment 2 has nozzle B26 and nozzle B26*b*. That is, the mist-generating device according to Variation 2 of Embodiment 2 has a plurality of nozzles.

Nozzle B26*b* is a nozzle for generating multilayer mist BM1 containing second liquid L2 having a different thickness than second liquid L2 of multilayer mist BM. Second discharging port B29*b* of nozzle B26 and second discharging port B29*bb* of nozzle B26*b* have different bore diameters. Specifically, the plurality of nozzles B26 and B26*b* have first discharging port B29*a* having the same bore diameter, that is, have the first nozzle part having the same outer diameter, but the plurality of nozzles B26 and B26*b* have second discharging ports B29*b* and B29*bb* having different bore diameters R1 and R2, respectively. FIG. 18 illustrates a case where bore diameter R1 of second discharging port B29*b* of nozzle B26 is smaller than bore diameter R2 of second discharging port B29*bb* of nozzle B26*b*.

Although not shown, first discharging port B29*a* of nozzle B26*b* is in communication with first accommodation unit B11 via the channel in nozzle B26 so that first liquid L1 can move therebetween. Second discharging port B29*bb* of nozzle B26*b* is in communication with second accommodation unit B12 via the channel in nozzle B26 so that second liquid L2 can move therebetween.

Unlike first electrode B30, a plurality of through-holes B32 are formed in first electrode B30*a*. The plurality of through-holes B32 pass through flat plate part B31 in the thickness direction (that is, the back-and-forth direction). The plurality of through-holes B32 are formed at locations opposed to nozzles B26 and B26*b*.

FIG. 18 shows two nozzles B26 and B26*b*. The same number of through-holes B32 as the plurality of nozzles are formed in flat plate part B31.

As described above, the mist-generating device according to Variation 2 of Embodiment 2 has a plurality of nozzles. The plurality of nozzles (nozzles B26 and B26*b*, for example) have second discharging ports of different bore diameters (bore diameters R1 and R2, for example).

With such a configuration, provided that the first nozzle parts have the same outer diameter, the mist-generating device according to Variation 2 of Embodiment 2 can generate a plurality of multilayer mists each containing a film of second liquid L2 having a different thickness (multilayer mists BM and BM1 shown in FIG. 9, for example) at the same time. That is, the mist-generating device according to Variation 2 of Embodiment 2 can generate a plurality of multilayer mists BM and BM1 that can float in the air for different lengths of time at the same time. Therefore, the mist-generating device according to Variation 2 of Embodiment 2 is likely to uniformly generate multilayer mists BM and BM1 in a predetermined space.

Note that, in the mist-generating device according to Embodiment 2, for example, first accommodation unit B11 may accommodate third liquid L3 containing functional droplet L generated by mist-generating unit 400 shown in FIG. 1, and second accommodation unit B12 may accommodate a fourth liquid that differs from third liquid L3 in liquid properties (oily or aqueous). In other words, one of third liquid L3 and the fourth liquid is oily, and the other is aqueous.

For example, the mist-generating device includes nozzle B26 that discharges third liquid L3 containing functional droplet L, and first electrode B30 that is arranged to be opposed to nozzle B26 and applies a voltage to third liquid L3 containing functional droplet L discharged from nozzle B26 to atomize third liquid L3 containing functional droplet L to generate a multilayer mist. Nozzle B26 may have inner first discharging port B29*a* and outer second discharging port B29*b* that are concentrically formed, and the control unit may control first discharging port B29*a* to discharge third liquid L3 containing functional droplet L and second discharging port B29*b* to discharge a fourth liquid having a lower volatility than third liquid L3 so as to generate a multilayer mist containing third liquid L3 having a spherical shape and the fourth liquid covering the whole of third liquid L3.

With such a configuration, the mist-generating device can more simply generate a multilayer mist containing a plurality of liquid layers.

EMBODIMENT 3

In the following, a mist-generating device according to Embodiment 3 will be described. The description of the mist-generating device according to Embodiment 3 will be focused on differences from mist-generating device 100 according to Embodiment 1. In the description of the mist-generating device according to Embodiment 3, the components that are substantially the same as those of mist-generating device 100 according to Embodiment 1 are denoted by the same reference numerals, and descriptions thereof may be simplified or omitted.

Figure 19:
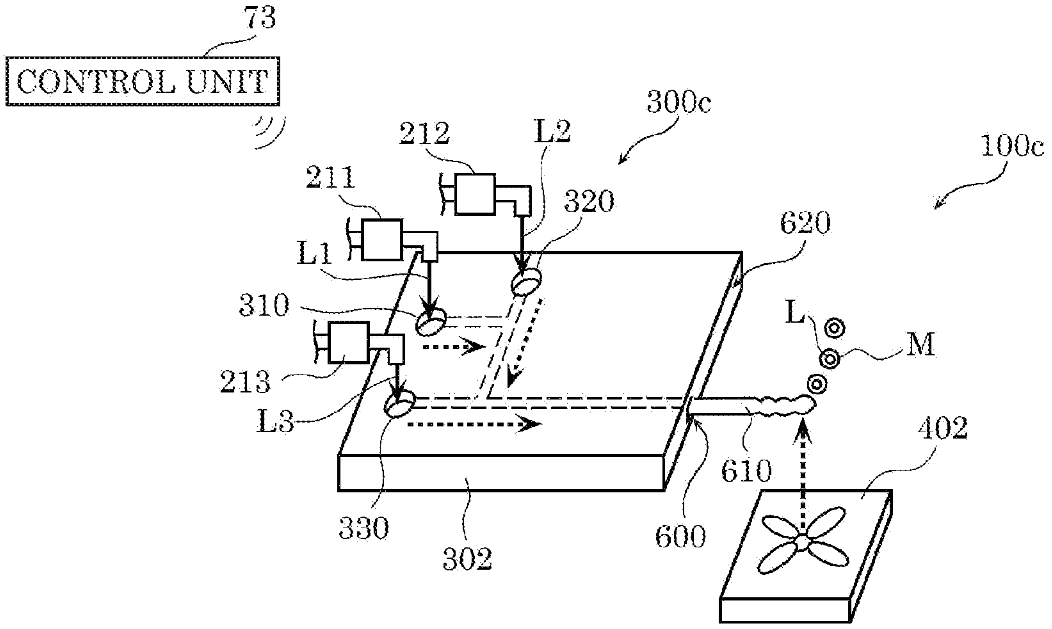
FIG. 19 is a schematic perspective view showing a configuration of a mist-generating device according to Embodiment 3.

FIG. 19 is a schematic perspective view showing a configuration of mist-generating device 100*c* according to Embodiment 3.

As shown in FIG. 19, mist-generating device 100*c* includes droplet generating unit 300*c* and mist-generating unit 402.

Droplet generating unit 300*c* includes microchannel chip 302, which is a microfluidic device that has a channel having a size of the order of micrometers and generates functional droplet L in third liquid L3, and supplying units 211, 212, and 213 that supply first liquid L1, second liquid L2, and third liquid L3 to microchannel chip 302.

Microchannel chip 302 is a plate-like body in which a channel is formed through which first liquid L1, second liquid L2, and third liquid L3 pass. The channel of microchannel chip 302 branches in a T-shaped and/or X-shaped configuration. In this embodiment, as with microchannel chip 301 shown in FIG. 4, microchannel chip 302 has first liquid channel 311 (see FIG. 4) through which first liquid L1 passes, second liquid channel 321 (see FIG. 4) through which second liquid L2 passes, mixing channel 322 (see FIG. 4) that is connected to first liquid channel 311 and second liquid channel 321 and allows the whole of first liquid L1 to be covered by second liquid L2, and third liquid channel 331 (see FIG. 4) that is connected to mixing channel 322 and allows the whole of first liquid L1 and second liquid L2 to be covered by third liquid L3. Microchannel chip 302 has discharging port 600 that is connected to third liquid channel 331 and discharges third liquid L3 containing functional droplet L having passed through third liquid channel 331 to the outside of microchannel chip 302.

Discharging port 600 is a hole formed in microchannel chip 302 for discharging third liquid L3 containing functional droplet L having passed through third liquid channel 331 to the outside of microchannel chip 302.

In this embodiment, microchannel chip 302 is a plate-like body, and discharging port 600 is formed in a side surface (discharging surface 620) of microchannel chip 302. Discharge liquid 610, which is third liquid L3 containing functional droplet L, is discharged from discharging port 600.

Microchannel chip 302 is made of a glass material or a resin material, for example.

Discharging surface 620 of microchannel chip 302 has a water repellency, for example.

Therefore, discharge liquid 610 is difficult to adhere to discharging surface 620. As a result, discharge liquid 610 is likely to spurt from discharging port 600, rather than dripping.

Mist-generating unit 402 is a device that generates multilayer mist M by atomizing third liquid L3 containing functional droplet L generated by microchannel chip 302. In this embodiment, mist-generating unit 402 is an air blower that blows air.

For example, mist-generating unit 402 blows air vertically upward. Microchannel chip 302 is arranged above mist-generating unit 402 in the vertical direction, and horizontally discharges discharge liquid 610 from discharging port 600 to directly above mist-generating unit 402.

Figure 20:
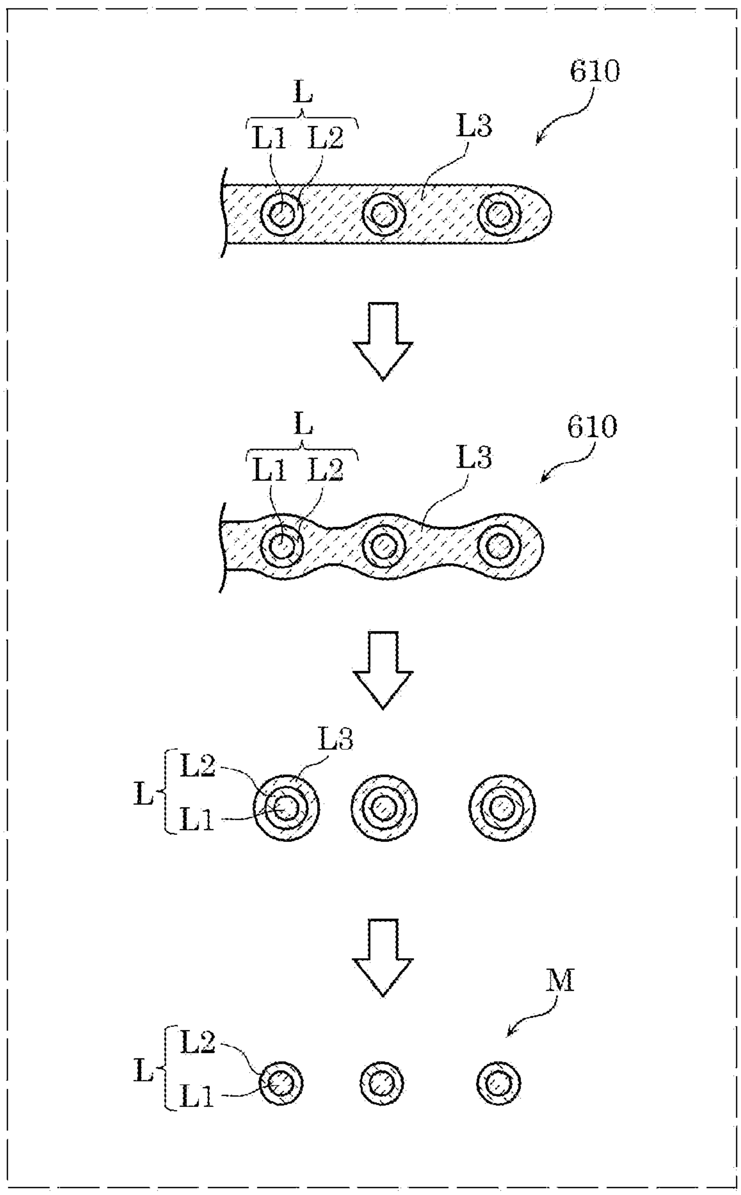
FIG. 20 is a diagram schematically showing how a multilayer mist is generated by the mist-generating device according to Embodiment 3.

FIG. 20 is a diagram schematically showing how multilayer mist M is generated by mist-generating device 100*c* according to Embodiment 3.

As for the setting of the pressure under which discharge liquid 610 is horizontally discharged from discharging port 600, control unit 73 sets the discharge pressure so that discharged third liquid L3 containing functional droplet L forms a liquid column by controlling the amount of first liquid L1, second liquid L2, and/or third liquid L3 supplied per unit time to microchannel chip 302 by supplying unit 211, 212, and/or 213.

The liquid column becomes slightly constricted in parts between particles of second liquid L2, which has a relatively low volatility and a relatively high viscosity.

The liquid column becomes further constricted because of the surface tension and eventually splits into a plurality of parts, and third liquid L3 volatilizes. In this way, multilayer mist M with second liquid L2 exposed to the air is formed.

To promote the splitting of such fine liquid columns, mist-generating unit 402 blows air from below to discharge liquid 610 forming the liquid columns. Thus, the efficiency of the atomization of discharge liquid 610 can be increased. In addition, multilayer mist M is discharged upward in a controlled manner by the action of the blown air, so that the floating time of multilayer mist M can be extended.

Control unit 73 is a control device that controls the overall operation of mist-generating device 100*c*. Specifically, control unit 73 controls operations of mist-generating unit 402 and supplying units 211, 212, and 213, for example. For example, control unit 73 controls mist-generating unit 402, thereby controlling the timing of air-blow of mist-generating unit 402 and the magnitude of the wind, for example.

Control unit 73 is implemented by a microcontroller, for example. Specifically, control unit 73 is implemented by a nonvolatile memory storing a program, a volatile memory used as a temporary storage area for execution of the program, an input/output port, a processor that executes the program, and the like. Control unit 73 may be implemented by a dedicated electronic circuit that realizes each operation.

Note that control unit 73 has only to be able to control mist-generating unit 402 and supplying units 211, 212, and 213, and may control mist-generating unit 402 and supplying units 211, 212, and 213 by transmitting a radio signal or may be connected to mist-generating unit 402 and supplying units 211, 212, and 213 by a control line or the like.

Note that microchannel chip 302 shown in FIG. 19 does not have reservoir 340 shown in FIG. 4. When a mist-generating unit atomizes third liquid L3 containing functional droplet L by electrostatic atomization or ultrasonic vibration, an amount of third liquid L3 containing functional droplet L equal to or greater than the predetermined amount is needed. However, mist-generating device 100*c* generates multilayer mist M by atomizing third liquid L3 containing functional droplet L by blowing air to discharge liquid 610 discharged from microchannel chip 302, and therefore can atomize a small amount of third liquid L3 containing functional droplet L. Therefore, any accommodation unit that accommodates third liquid L3 containing functional droplet L, such as reservoir 340 shown in FIG. 4, can be omitted. Therefore, microchannel chip 302 can be reduced in size. In addition, by using microchannel chip 302, each single particle of multilayer mist M can be separately generated. Therefore, with mist-generating device 100*c*, multilayer mist M does not need to be charged, unlike the case where multilayer mist M is generated by electrostatic atomization. Therefore, voltage applying unit 40 shown in FIG. 1 or other similar components can be omitted. Therefore, mist-generating device 100*c* can be expected to be further reduced in size.

A portion of discharging surface 620 around discharging port 600 preferably projects in the direction in which discharge liquid 610 is discharged.

Figure 21:
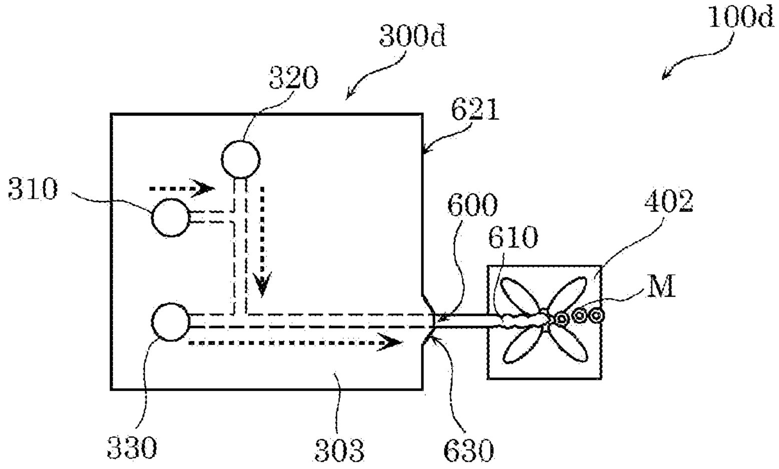
FIG. 21 is a top view showing a configuration of a mist-generating device according to Variation 1 of Embodiment 3.

FIG. 21 is a top view showing a configuration of mist-generating device 100*d* according to Variation 1 of this embodiment. In FIG. 21, illustration of some components of mist-generating device 100*d*, such as control unit 73, supplying units 211 to 213, is omitted.

As shown in FIG. 21, mist-generating device 100*d* differs from mist-generating device 100*c* in configuration of microchannel chip 303 of droplet generating unit 300*d*.

Discharging surface 621, which is a side surface of microchannel chip 303 in which discharging port 600 is formed, projects in the direction in which discharge liquid 610 is discharged at a portion around discharging port 600. Specifically, inclined portion 630, which has a surface inclined toward the direction in which discharge liquid 610 is discharged, is formed on discharging surface 621. As a result, discharge liquid 610 is unlikely to adhere to discharging surface 621, compared with the case where inclined portion 630 is not formed.

Note that, although FIG. 21 shows inclined portion 630, which is a portion around discharging port 600 that projects in the direction in which discharge liquid 610 is discharged in top view, the part where inclined portion 630 is formed is not limited thereto.

For example, inclined portion 630 may be formed in such a manner that the inclined surface around discharging port 600 projects in the direction in which discharge liquid 610 is discharged in side view of microchannel chip 303 (that is, when viewed from the direction that is parallel with the principal surface (upper surface) of microchannel chip 303 and is parallel with discharging surface 621).

Although mist-generating unit 402 has been described as an air blower as an example, mist-generating unit 402 has only to be able to atomize discharge liquid 610 and is not limited to the air blower. For example, mist-generating unit 402 may be a vibration generating device that atomizes discharge liquid 601 by causing vibrations of microchannel chip 302 or 303.

(Other Embodiments)

Although mist-generating devices according to the present invention have been described with regard to various embodiments and variations thereof, the present invention is not limited to the embodiments and variations described above.

For example, in the embodiments described above, multilayer mist M is charged by electrostatic atomization or by charging electrode 30*a* shown in FIG. 8. However, in order to charge multilayer mist M, third liquid L3 yet to be atomized may be charged in advance. That is, multilayer mist M may be generated by charging third liquid L3 containing functional droplet L generated by droplet generating unit 300 and atomizing charged third liquid L3 containing functional droplet L.

According to such a method, atomization and charging of third liquid L3 containing functional droplet L can be separately performed, so that the amount of multilayer mist M generated and the amount of charge of multilayer mist M can be separately controlled. Therefore, according to such a method, the amount of multilayer mist M generated can be controlled to a desired amount.

The process of charging third liquid L3 is not particularly limited. For example, an electrode electrically connected to the voltage applying unit may be arranged in container 10, and a voltage may be applied to the electrode to charge third liquid L3 in container 10. Note that the predetermined voltage applied by the voltage applying unit may be a pulse voltage, a pulsating voltage, or an alternating-current voltage.

Multilayer mist M does not always need to be charged with electric charge E. According to the concept of the present invention, the mist-generating device may not charge multilayer mist M with electric charge E.

For example, in the embodiments described above, an example has been shown in which electrode support plate 21 is arranged to cover the top surface of third liquid L3, and nozzle 26 projects in an upward direction. However, the present invention is not limited thereto. For example, electrode support plate 21 may cover the bottom surface or side surface of third liquid L3, and a plurality of nozzles 26 may project in a downward direction, a sideward direction, or a slanting direction. The direction in which the mist-generating device according to the present invention sprays multilayer mist M is not limited to the upward direction but can be the downward direction, the sideward direction, or the slanting direction.

For example, electrode support plate 21 and nozzle 26 of ejection plate 20 may be integrally formed. Ejection plate 20 may be integrally formed by injection molding of a metal material or a resin material, for example.

For example, first electrode 30 may not be a flat plate-shaped electrode and may be an electrode plate smoothly curved, for example. Through-hole 32 may pass through the electrode plate in the thickness direction or pass through the electrode plate in the direction in which nozzle 26 projects.

For example, in the embodiments described above, droplet generating units 300, 300*a*, and 300*b* generate functional droplet L in third liquid L3. The mist-generating device may generate functional droplet L in third liquid L3 by the droplet generating unit first generating functional droplet L and the supplying unit then supplying functional droplet L into third liquid L3.

For example, in the embodiments described above, supplying unit 210 is a pump, and functional droplet L generated by droplet generating unit 300 is supplied to third liquid L3 in container 10 by supplying unit 210. For example, when droplet generating unit 300 is arranged on top of container 10, and the amount of first liquid L1 and second liquid L2 introduced to microchannel chip 301 is controlled by control unit 70, that is, when control unit 70 controls the generation of functional droplet L, the supplying unit may be piping that introduces functional droplet L generated by droplet generating unit 300 into third liquid L3 in container 10.

For example, in the embodiments described above, an example has been shown in which electrode support plate 21 is arranged to cover the top surface of first liquid L1 and second liquid L2, and nozzle B26 projects in an upward direction. However, the present invention is not limited thereto. For example, electrode support plate 21 may cover the bottom surface or side surface of first liquid L1 and second liquid L2, and nozzle B26 may projects in a downward direction, a sideward direction, or a slanting direction. The direction in which mist-generating device B100 according to the present invention sprays multilayer mist BM is not limited to the upward direction but can be the downward direction, the sideward direction, or the slanting direction.

For example, electrode support plate B21 and nozzle B26 of ejection plate B20 may be integrally formed. Ejection plate B20 may be integrally formed by injection molding of a metal material or a resin material, for example.

For example, first electrode B30 may not be a flat plate-shaped electrode and may be an electrode plate smoothly curved, for example. Through-hole B32 may pass through the electrode plate in the thickness direction or pass through the electrode plate in the direction in which nozzle B26 projects.

For example, in the embodiments described above, nozzle B26 includes first nozzle part B27, and second nozzle part B28 that covers the outer periphery of first nozzle part B27 at a distance. Nozzle B26 may include a third nozzle part that covers the outer periphery of second nozzle part B28 at a distance. With such a configuration, first liquid L1 can be covered by multiple layers of liquid.

For example, the mist-generating device may further include a conventional so-called single-layer nozzle having one discharging port, in addition to nozzle B26 in which first discharging port B29*a* and second discharging port B29*b* are formed.

For example, first liquid L1 may be an aqueous liquid containing hypochlorous acid having a disinfection or other effect, or an oily liquid containing a perfume, for example. For example, second liquid L2 may also be an aqueous liquid containing hypochlorous acid having a disinfection or other effect, or an oily liquid containing a perfume, for example.

The thickness of second liquid L2 in multilayer mist BM may be appropriately modified according to conditions, such as the rate of volatilization of second liquid L2, the weight of multilayer mist BM, or the temperature, humidity, composition of the air. The thickness of second liquid L2 can be set so that second liquid L2 volatilizes or is lost to expose first liquid L1 to the air until multilayer mist BM reaches to a predetermined distance, which is arbitrarily determined in advance.

For example, the mist-generating device may be provided with an air blower having a fan or the like, in order to make the generated multilayer mist travel far or fix the direction of travel of the generated multilayer mist.

Furthermore, in the foregoing embodiments, all of the elements such as controller 70 may be configured using dedicated hardware, or may be implemented by executing software programs suitable for the respective elements. Each of the elements may be implemented by a program executing component, such as a central processing unit (CPU) or processor, reading and executing a software program recorded on a recording medium such as a hard disk drive (HDD) or a semiconductor memory.

Furthermore, elements such as controller 70 may be configured using one or more electronic circuits. The one or more electronic circuits may each be a general-purpose circuit or a dedicated circuit.

The one or more electronic circuits may include, for example, a semiconductor device, an integrated circuit (IC), or a large-scale integration (LSI). The IC or LSI may be integrated in a single chip or several chips. Although referred to here as IC or LSI, the name may change depending on the scale of integration, and may be referred to as a system LSI, very large scale integration (VLSI), or ultra large scale integration (ULSI). Furthermore, a field programmable gate array (FPGA) that can be programmed after being manufactured may be used for the same purpose.

Furthermore, general or specific aspects of the present invention may be implemented as a system, an apparatus, a method, an integrated circuit, a computer program, or a non-transitory computer-readable recording medium such as an optical disc, an HDD, or a semiconductor memory on which the computer program is recorded, or may be implemented as any combination of a system, an apparatus, a method, an integrated circuit, a computer program, and a recording medium.

Aside from the foregoing, forms obtained by various modifications to the respective embodiments that may be conceived by a person of skill in the art as well as forms realized by arbitrarily combining structural components and functions in the respective embodiments without departing from the spirit of the present invention are also included in the present invention.

The invention claimed is:

1. A mist-generating device, comprising:

a droplet generating unit configured to generate, in a third liquid, a functional droplet including a first liquid that is spherical and a second liquid that covers an entirety of the first liquid and has a volatility lower than a volatility of the first liquid; and a mist-generating unit configured to generate a multilayer mist obtained by atomizing the third liquid containing the functional droplet into a mist, wherein the droplet generating unit is a microchannel chip including:

a first liquid channel through which the first liquid passes;

a second liquid channel through which the second liquid passes;

a mixing channel connected to the first liquid channel and the second liquid channel, for covering the entirety of the first liquid with the second liquid; and a third liquid channel connected to the mixing channel, for covering an entirety of the first liquid and the second liquid with the third liquid.

2. The mist-generating device according to claim 1, further comprising:

a supplying unit configured to supply the third liquid containing the functional droplet generated by the droplet generating unit to the mist-generating unit.

3. The mist-generating device according to claim 1, wherein the second liquid is one of a biomaterial and a biocompatible material.

4. The mist-generating device according to claim 1, wherein one of the first liquid and the second liquid is oily and the other of the first liquid and the second liquid is aqueous.

5. The mist-generating device according to claim 1, wherein the third liquid has a volatility higher than the volatility of the second liquid.

6. The mist-generating device according to claim 1, wherein the functional droplet has a particle size of at most 10 μm.

7. The mist-generating device according to claim 1, wherein the mist-generating unit is an ultrasonic vibration generator configured to generate the multilayer mist by atomizing the third liquid containing the functional droplet by applying an ultrasonic vibration to the third liquid containing the functional droplet.

8. The mist-generating device according to claim 1, further comprising:

a charging electrode for charging the multilayer mist.

9. The mist-generating device according to claim 1, wherein the mist-generating unit includes:

a nozzle configured to discharge the third liquid containing the functional droplet; and a first electrode disposed opposite to the nozzle and configured to generate the multilayer mist by atomizing the third liquid containing the functional droplet by applying a voltage to the third liquid containing the functional droplet discharged from the nozzle.

* * * * *